United States Patent
Beidler et al.

(10) Patent No.: US 10,618,974 B2
(45) Date of Patent: Apr. 14, 2020

(54) ANTI-TRKA ANTIBODY

(71) Applicant: Eli Lilly and Company, Indianapolis, IN (US)

(72) Inventors: Catherine Brautigam Beidler, Poway, CA (US); Daniel Scott Girard, San Diego, CA (US); Chetankumar Natvarlal Patel, Fishers, IN (US)

(73) Assignee: Eli Lilly and Company, Indianapolis, IN (US)

( * ) Notice: Subject to any disclaimer, the term of this patent is extended or adjusted under 35 U.S.C. 154(b) by 0 days.

(21) Appl. No.: 16/281,227

(22) Filed: Feb. 21, 2019

(65) Prior Publication Data

US 2019/0263932 A1    Aug. 29, 2019

Related U.S. Application Data

(60) Provisional application No. 62/636,207, filed on Feb. 28, 2018.

(51) Int. Cl.

| A61K 39/395 | (2006.01) |
| C07K 16/28 | (2006.01) |
| C07K 16/40 | (2006.01) |
| A61P 29/02 | (2006.01) |
| A61K 39/00 | (2006.01) |

(52) U.S. Cl.
CPC .............. *C07K 16/40* (2013.01); *A61P 29/02* (2018.01); *C07K 16/2863* (2013.01); *A61K 2039/505* (2013.01); *C07K 2317/51* (2013.01); *C07K 2317/515* (2013.01); *C07K 2317/56* (2013.01); *C07K 2317/565* (2013.01); *C07K 2317/76* (2013.01); *C07K 2317/92* (2013.01)

(58) Field of Classification Search
None
See application file for complete search history.

(56) References Cited

U.S. PATENT DOCUMENTS

| 5,844,092 A | 12/1998 | Presta et al. |
| 6,610,500 B1 | 8/2003 | Saragovi et al. |
| 7,449,616 B2 | 11/2008 | Pons et al. |
| 7,601,352 B1 | 10/2009 | Novak |
| 7,601,818 B2 | 10/2009 | Wild, Jr. et al. |
| 7,988,966 B2 | 8/2011 | Pavone |
| 8,144,893 B2 | 3/2012 | Sherman |
| 8,296,079 B2 | 10/2012 | Cattaneo et al. |
| 8,642,040 B2 | 2/2014 | Mi et al. |
| 8,728,473 B2 | 5/2014 | Garcia-Martinez et al. |
| 9,365,654 B2 | 6/2016 | Rovati et al. |
| 9,517,238 B2 | 12/2016 | Rochman et al. |
| 9,688,749 B2 | 6/2017 | Pavone et al. |
| 9,751,947 B2 | 9/2017 | Benigni et al. |
| 10,100,121 B2 | 10/2018 | Fanslow, III et al. |
| 10,208,125 B2 | 2/2019 | Schoen et al. |
| 10,219,998 B2 | 3/2019 | Lieberman et al. |
| 2002/0169154 A1 | 11/2002 | Ruggeri et al. |
| 2003/0157099 A1 | 8/2003 | Presta |
| 2004/0058416 A1 | 3/2004 | Presta |
| 2006/0058250 A1 | 3/2006 | Denmeade |
| 2006/0275797 A1 | 12/2006 | Shephard |
| 2011/0077293 A1 | 3/2011 | Ye |
| 2013/0336961 A1 | 12/2013 | Popovich et al. |
| 2013/0336964 A1 | 12/2013 | Rovati et al. |
| 2013/0344064 A1 | 12/2013 | Blein et al. |
| 2014/0316113 A1 | 10/2014 | Cattaneo et al. |
| 2015/0073036 A1 | 3/2015 | Hawryluk et al. |
| 2017/0258871 A1 | 9/2017 | Toillon et al. |
| 2017/0306013 A1 | 10/2017 | Clark et al. |
| 2017/0362327 A1 | 12/2017 | Walmsley et al. |
| 2019/0000840 A1 | 1/2019 | Li et al. |
| 2019/0184015 A1 | 6/2019 | Heppenstall et al. |

FOREIGN PATENT DOCUMENTS

| AU | 2014277649 A1 | 12/2014 |
| EP | 471205 A1 | 7/1991 |
| JP | 2012201621 A2 | 10/2012 |
| NZ | 501161 | 3/1995 |
| WO | 2000/73344 A2 | 12/2000 |
| WO | 2007035906 A2 | 3/2007 |
| WO | 2008006893 A1 | 1/2008 |
| WO | 2013026021 A2 | 2/2013 |
| WO | 2016/087677 A1 | 6/2016 |
| WO | 2016146730 A1 | 9/2016 |

OTHER PUBLICATIONS

Price, Eric, et al, J Neurosci Methods 282:34-42, 2017.
Written Opinion of the International Searching Authority, dated Jul. 17, 2019.
International Searching Authority, Notification of Transmittal of The International Search Report and The Written Opinion of the International Searching Authority, or the Declaration, dated Jul. 17, 2019.

(Continued)

*Primary Examiner* — Christine J Saoud
*Assistant Examiner* — Jon M Lockard
(74) *Attorney, Agent, or Firm* — Kyle W Grimshaw

(57) ABSTRACT

Antibodies to tropomysin receptor kinase (TrkA), compositions including such antibodies, and methods of using such antibodies for the treatment of pain including post-surgical pain, rheumatoid arthritis pain, neuropathic pain and osteoarthritis pain.

20 Claims, No Drawings
Specification includes a Sequence Listing.

(56) References Cited

OTHER PUBLICATIONS

Ugolini Gabriele et al: "The function neutralizing anti-TrkA antibody MNAC13 reduces inflammatory and neuropathic pain", PNAS, National Academy of Sciences, US, vol. 104, No. 8, Feb. 20, 2007 (Feb. 20, 2007), pp. 2985-2990, XP002569601, ISSN: 0027-8424, DOI: 10.1073/PNAS.061153104.

Anna E. Rapp et al: "Analgesia via blockade of NGF/TrkA signaling does not influence fracture healing in mice", Journal of Orthopaedic Research, vol. 33, No. 8, May 7, 2015 (May 7, 2015), pp. 1235-1241, XP055251059, US, ISSN: 0736-0266, DOI: 10.1002/jor.22892.

Covaceuszach S et al: "Neutralization of NGF-TrkA receptor interaction by the novel antagonistic anti-TrkA monoclonal antibody, MNAC13: a structural insight", Proteins: Structure, Function, and Bioinformatics, John Wiley & Sons, Inc, US, vol. 58, No. 3, Feb. 15, 2005 (Feb. 15, 2005), pp. 717-727, XP002338675, ISSN: 0887-3585, DOI: 10.1002/PROT.20366.

ANTI-TrKA ANTIBODY

The present invention is in the field of medicine. Particularly, the present invention relates to antibodies to tropomysin receptor kinase A (TrkA), compositions comprising such anti-TrkA antibodies, and methods of using such antibodies for the treatment of pain. The antibodies and methods of using the same may treat acute or chronic pain of nociceptive/inflammatory, neuropathic, nociplastic, or mixed etiologies. In other embodiments, the antibodies and methods may be used to treat acute or chronic pain that is musculoskeletal or neuropathic in origin. Specific, non-limiting examples of pain include, for example, post-surgical pain, rheumatoid arthritis pain, osteoarthritis pain, neuropathic pain, diabetic neuropathic pain (DNP), and chronic lower back pain (CLBP), including non radicular (non-neuropathic) and radicular lower back pain (which are sometimes referred to as lumbosacral radiculopathy (LSR) or sciatica) as well as visceral pain (such as, for example, chronic prostatitis, interstitial cystitis (bladder pain) or chronic pelvic pain).

U.S. Patent Application Publication No. 2013/0336964 explains the role of TrkA and Nerve Growth Factor (NGF) in the human pain system. Specifically, in certain situations, NGF will bind to and activate the TrkA protein as part of the pain pathway in the body. This binding potentiates pain signaling through multiple mechanisms. (See WO 2016/087677). Accordingly, targeting NGF can potentially be useful in treating pain, and inflammation-related pain can be significantly reduced by neutralizing NGF bioactivity in animal models. (See, for example, WO 2016/087677; and U.S. Pat. No. 7,449,616). U.S. Patent Application Publication No. 2013/0336961, U.S. Pat. No. 7,601,818, WO 2000/73344 and WO 2016/087677 recite various antibodies that are designed to bind to TrkA. The protein sequence for human TrkA is provided in U.S. Patent Application Publication No. 2013/0336961.

Persistent pain represents a major health problem and causes significant losses in quality of life. Persistent pain may present with different levels of severity, and is associated with a variety of pathologies, such as back injury or degenerative disk disease, migraine headaches, arthritis, diabetic neuropathy, cancer and other diseases. Mild pain is presently treated with acetaminophen, aspirin, and other (typically over-the-counter) medications. Moderate pain may be controlled using corticosteroidal drugs such as cortisol and prednisone. Problems with the effectiveness and/or tolerability of existing treatments are well known, and corticosteroids for example display remarkable adverse effects including weight gain, insomnia, and immune system weakening. Moderate or severe pain may be treated with opioids such as morphine and fentanyl, but long-term use of opiates is limited by several serious drawbacks, including development of addiction, tolerance and physical dependence. Potential overuse of opioids has been characterized as an "opioid epidemic" in view of the growing number of people that use and may be addicted to opioids.

As current pain therapies are often poorly effective and/or have serious undesirable side effects, an urgent need exists to develop drugs which are directed to new molecular targets and may provide a combination of improved pharmacological properties, including safety, potency, efficacy, and tolerability, in particular for the treatment of chronic pain. To date, no agents targeting TrkA signaling have been approved for the treatment of pain. Thus, there remains a need for agents that can inhibit TrkA signaling, such as alternative anti-TrkA antibodies. There is also a need for such an agent that provides a therapeutic benefit.

The present invention provides antibodies that bind TrkA and which comprises a heavy chain variable region (HCVR) and a light chain variable region (LCVR), wherein the HCVR comprises the complementarity determining regions (CDRs) HCDR1, HCDR2 and HCDR3, and the LCVR comprises CDRs LCDR1, LCDR2 and LCDR3, wherein the amino acid sequence of HCDR1 is SEQ ID NO: 3, the amino acid sequence of HCDR2 is SEQ ID NO: 4, the amino acid sequence of HCDR3 is SEQ ID NO: 5, the amino acid sequence of LCDR1 is SEQ ID NO: 7, the amino acid sequence of LCDR2 is SEQ ID NO: 8, and the amino acid sequence of LCDR3 is SEQ ID NO: 9. As noted below, the amino acid sequence of the LCDR1 of SEQ ID NO: 7 includes an $X_{aa}$ at residue 10 that is one of N, A or Q. In some of the presently preferred embodiments, $X_{aa}$ at position 10 of SEQ ID NO: 7 is A. In other of the presently preferred embodiments, $X_{aa}$ at position 10 of SEQ ID NO: 7 is Q.

Embodiments of the present invention provide an antibody that binds TrkA, comprising a HCVR and a LCVR, wherein the amino acid sequence of the HCVR is SEQ ID NO: 10 and the amino acid sequence of the LCVR is SEQ ID NO: 11. As noted below, the amino acid sequence of the LCVR of SEQ ID NO: 11 includes an $X_{aa}$ at residue 33 that is one of N, A or Q. In some of the presently preferred embodiments, $X_{aa}$ at residue 33 of SEQ ID NO: 11 is A. In other presently preferred embodiment, $X_{aa}$ at residue 33 of SEQ ID NO: 11 is Q.

In further embodiments, the present invention provides an antibody that binds TrkA, comprising a heavy chain (HC) and a light chain (LC), wherein the amino acid sequence of the HC is selected from the group consisting of SEQ ID NO: 1 and SEQ ID NO: 2 and the amino acid sequence of the LC is SEQ ID NO: 6. As noted below, the amino acid sequence of the LC defined in SEQ ID NO: 6 includes an $X_{aa}$ at residue 33 that is one of N, A or Q. In some of the presently preferred embodiments, $X_{aa}$ at residue 33 of SEQ ID NO: 6 is A. In other presently preferred embodiments, $X_{aa}$ at residue 33 of SEQ ID NO: 6 is Q. In some embodiments, there are two HCs and two LCs, wherein each of the LCs have the amino acid sequence of SEQ ID NO: 6 and each of the HCs have the amino acid sequence of either SEQ ID NO: 1 or SEQ ID NO: 2.

The various embodiments of the LC of SEQ. ID NO: 6 may be used either with the HC of SEQ ID NO: 1 or the HC of SEQ ID NO: 2. In one embodiment, the HC is defined by SEQ ID NO: 1 and the LC of SEQ ID NO: 6 is constructed such that $X_{aa}$ at residue 33 of SEQ ID NO: 6 is Q. In another embodiment, the HC is defined by SEQ ID NO: 1 and the LC of SEQ ID NO: 6 is constructed such that $X_{aa}$ at residue 33 of SEQ ID NO: 6 is A. In a further embodiment, the HC is defined by SEQ ID NO: 2 and the LC of SEQ ID NO: 6 is constructed such that $X_{aa}$ at residue 33 of SEQ ID NO: 6 is Q. In yet an additional embodiment, the HC is defined by SEQ ID NO: 2 and the LC of SEQ ID NO: 6 is constructed such that $X_{aa}$ at residue 33 of SEQ ID NO: 6 is A.

The present invention further provides pharmaceutical compositions comprising an antibody of the present invention and one or more pharmaceutically acceptable carriers, diluents or excipients. Further, the present invention provides a method of treating pain comprising administering to a patient in need thereof a pharmaceutical composition of the present invention. In an even further embodiment, the present invention provides a method of treating acute or chronic pain of nociceptive/inflammatory, neuropathic, nociplastic, or mixed etiologies. In other embodiments, the pain is acute or chronic pain that is musculoskeletal or neuropathic in origin. Specific, non-limiting examples of pain that may be treated by the present embodiments include, for example, post-surgical pain, rheumatoid arthritis pain, neuropathic pain, and osteoarthritis pain. (As used herein, osteoarthritis pain expressly includes non radicular (non-neuropathic) pain. As used herein, neuropathic pain expressly includes radicular pain CLBP, DNP, and LSR.) In some embodiments, the pain is chronic pain, such as for example, chronic pain of both musculoskeletal as well as neuropathic origin. In other embodiments, the pain visceral pain (such as, for example, chronic prostatitis, interstitial cystitis (bladder pain) or chronic pelvic pain).

In an even further embodiment, the present invention provides a method of treating pain comprising administering to a patient in need thereof a pharmaceutical composition of the present invention. In some embodiments, the pain is chronic pain, such as for example, chronic pain of both musculoskeletal as well as neuropathic origin.

In addition, the present invention provides a method of treating pain comprising administering to a patient in need thereof an effective amount of an antibody of the present invention. In more particular embodiments, the present invention provides a method of treating acute or chronic pain of nociceptive/inflammatory, neuropathic, nociplastic, or mixed etiologies. In other embodiments, the pain is acute or chronic pain that is musculoskeletal or neuropathic in origin. Specific, non-limiting examples of pain include post-surgical pain, rheumatoid arthritis pain, neuropathic pain and osteoarthritis pain, including, for example, non radicular (non-neuropathic) and radicular CLBP, DNP, and LSR, comprising administering to a patient in need thereof an effective amount of an antibody of the present invention. In some embodiments, method of treating involves treating pain that is chronic pain, such as for example, chronic pain of both musculoskeletal as well as neuropathic origin. In other embodiments, method of treating involves treating pain that visceral pain (such as, for example, chronic prostatitis, interstitial cystitis (bladder pain) or chronic pelvic pain).

The present invention also provides an antibody of the present invention for use in therapy. More particularly, the present invention provides an antibody of the present invention for use in treatment of pain. In particular embodiments, the present invention provides an antibody of the present invention for use in treatment of acute or chronic pain of nociceptive/inflammatory, neuropathic, nociplastic, or mixed etiologies, including but not limited to, post-surgical pain, neuropathic pain, rheumatoid arthritis pain and osteoarthritis pain, including, for example, non radicular (non-neuropathic) and radicular CLBP, DNP, and LSR. In some embodiments, the antibody of the present invention is for use in treatment of pain that is chronic or acute pain, such as for example, chronic pain of both musculoskeletal as well as neuropathic origin. In other embodiments, the antibody of the present invention is for use in treatment of pain that is visceral pain (such as, for example, chronic prostatitis, interstitial cystitis (bladder pain) or chronic pelvic pain).

Further, the present invention provides the use of an antibody of the present invention is used in the manufacture of a medicament for the treatment of acute or chronic pain of nociceptive/inflammatory, neuropathic, nociplastic, or mixed etiologies, including but not limited to post-surgical pain, neuropathic pain, rheumatoid arthritis pain and osteoarthritis pain, including, for example, non radicular (non-neuropathic) and radicular CLBP, DNP, and LSR. In some such embodiments, the antibody of the present invention is used in the manufacture of a medicament for the treatment of pain that is acute or chronic pain, such as for example, chronic pain of both musculoskeletal as well as neuropathic origin. In other embodiments, the antibody of the present invention is used in the manufacture of a medicament for the treatment of pain visceral pain (such as, for example, chronic prostatitis, interstitial cystitis (bladder pain) or chronic pelvic pain).

The present embodiments also provide the use of an antibody that binds TrkA comprising a heavy chain variable region (HCVR) and a light chain variable region (LCVR), wherein the HCVR comprises complementarity determining regions (CDRs) HCDR1, HCDR2, and HCDR3 and the LCVR comprises CDRs LCDR1, LCDR2, and LCDR3, wherein the amino acid sequence of HCDR1 is SEQ ID NO: 3, the amino acid sequence of HCDR2 is SEQ ID NO: 4, the amino acid sequence of HCDR3 is SEQ ID NO; 5, the amino acid sequence of LCDR1 is SEQ ID NO: 7, the amino acid sequence of LCDR2 is SEQ ID NO: 8, and the amino acid sequence of LCDR3 is SEQ ID NO: 9, or a pharmaceutical composition comprising such an antibody, for the manufacture of a medicament for treating pain. In some embodiments, the antibody (or pharmaceutical composition comprising such an antibody) is used for the manufacture of a medicament for treating acute or chronic pain of nociceptive/inflammatory, neuropathic, nociplastic, or mixed etiologies, including but not limited to, post-surgical pain, rheumatoid arthritis pain, neuropathic pain and osteoarthritis pain, including, for example, non radicular (non-neuropathic) and radicular CLBP, DNP, and LSR, also known as sciatica. In other embodiments, the antibody (or pharmaceutical composition comprising such an antibody) is used for the manufacture of a medicament for treating chronic pain. In other embodiments, the antibody (or pharmaceutical composition comprising such an antibody) is used for the manufacture of a medicament for treating visceral pain (such as, for example, chronic prostatitis, interstitial cystitis (bladder pain) or chronic pelvic pain). In other embodiments, the antibody (or pharmaceutical composition comprising such an antibody) is used for the manufacture of a medicament for treating acute or chronic pain that is musculoskeletal or neuropathic in origin.

The present antibodies bind to TrkA. More specifically, the present antibodies may bind to TrkA such that NGF is blocked or prevented from binding to TrkA. Generally, NGF will bind to domain5 of TrkA receptor. However, the present antibodies may bind to TrkA and thereby block/prevent NGF from binding to all or a portion of the domain5 or another portion of TrkA.

Below are the sequences of some exemplary antibodies within the scope of the present embodiments:

An antibody having LC of SEQ ID NO: 6 (with $X_{aa}$ at residue 33 of SEQ ID NO: 6 being N) and HC of SEQ ID NO: 1 (hereinafter referred to as "mAb A"):

```
Light Chain
DIVMTQTPLSSPVTLGQPASISCRSSQSLVHRNGNTY

LSWLQQRPGQPPRLLIYKISNRFSGVPDRFSGSGAGT

DFTLKISRVEAEDVGVYYCMQARQFPLTFGGGTKVE

IKRTVAAPSVFIFPPSDEQLKSGTASVVCLLNNFYPRE

AKVQWKVDNALQSGNSQESVTEQDSKDSTYSLSST

LTLSKADYEKHKVYACEVTHQGLSSPVTKSFNRGEC
```

-continued

Heavy Chain
EVQLVESGGGLVKPGGSLRLSCAASGFTFSGVSINW

VRQAPGKGLEWVSSETTSSGTIYYADSVKGRFTISRD

NAKNSLYLQMNSLRAEDTAVYYCARSYYYGMDVW

GQGTTVTVSSASTKGPSVFPLAPCSRSTSESTAALGC

LVKDYFPEPVTVSWNSGALTSGVHTFPAVLQSSGLY

SLSSVVTVPSSSLGTKTYTCNVDHKPSNTKVDKRVE

SKYGPPCPPCPAPEAAGGPSVFLEPPKPKDTLMISRTP

EVTCVVVDVSQEDPEVQFNWYVDGVEVHNAKTKP

REEQFNSTYRVVSVLTVLHQDWLNGKEYKCKVSNK

GLPSSIEKTISKAKGQPREPQVYTLPPSQEEMTKNQV

SLTCLVKGFYPSDIAVEWESNGQPENNYKTTPPVLD

SDGSFFLYSRLTVDKSRWQEGNVFSCSVMHEALHN

HYTQKSLSLSLG

An antibody having LC of SEQ ID NO: 6 (with $X_{aa}$ at residue 33 of SEQ ID NO: 6 being A) and HC of SEQ ID NO: 1 (hereinafter referred to as "mAb B"):

Light Chain
DIVMTQTPLSSPVTLGQPASISCRSSQSLVHRAGNTY

LSWLQQRPGQPPRLLIYKISNRFSGVPDRFSGSGAGT

DFTLKISRVEAEDVGVYYCMQARQFPLTFGGGTKVE

IKRTVAAPSVFIFPPSDEQLKSGTASVVCLLNNFYPRE

AKVQWKVDNALQSGNSQESVTEQDSKDSTYSLSST

LTLSKADYEKHKVYACEVTHQGLSSPVTKSFNRGEC

Heavy Chain
EVQLVESGGGLVKPGGSLRLSCAASGFTFSGVSINW

VRQAPGKGLEWVSSETTSSGTIYYADSVKGRFTISRD

NAKNSLYLQMNSLRAEDTAVYYCARSYYYGMDVW

GQGTTVTVSSASTKGPSVFPLAPCSRSTSESTAALGC

LVKDYFPEPVTVSWNSGALTSGVHTFPAVLQSSGLY

SLSSVVTVPSSSLGTKTYTCNVDHKPSNTKVDKRVE

SKYGPPCPPCPAPEAAGGPSVFLFPPKPKDTLMISRTP

EVTCVVVDVSQEDPEVQFNWYVDGVEVHNAKTKP

REEQFNSTYRVVSVLTVLHQDWLNGKEYKCKVSNK

GLPSSIEKTISKAKGQPREPQVYTLPPSQEEMTKNQV

SLTCLVKGFYPSDIAVEWESNGQPENNYKTTPPVLD

SDGSFFLYSRLTVDKSRWQEGNVFSCSVMHEALHN

HYTQKSLSLSLG

An antibody having LC of SEQ ID NO: 6 (with $X_{aa}$ at residue 33 of SEQ ID NO: 6 being Q) and HC of SEQ ID NO: 1 (hereinafter referred to as "mAb C"):

Light Chain
DIVMTQTPLSSPVTLGQPASISCRSSQSLVHRQGNTY

LSWLQQRPGQPPRLLIYKISNRFSGVPDRFSGSGAGT

DFTLKISRVEAEDVGVYYCMQARQFPLTFGGGTKVE

IKRTVAAPSVFIFPPSDEQLKSGTASVVCLLNNFYPRE

AKVQWKVDNALQSGNSQESVTEQDSKDSTYSLSST

LTLSKADYEKHKVYACEVTHQGLSSPVTKSFNRGEC

Heavy Chain
EVQLVESGGGLVKPGGSLRLSCAASGFTFSGVSINW

VRQAPGKGLEWVSSETTSSGTIYYADSVKGRFTISRD

NAKNSLYLQMNSLRAEDTAVYYCARSYYYGMDVW

GQGTTVTVSSASTKGPSVFPLAPCSRSTSESTAALGC

LVKDYFPEPVTVSWNSGALTSGVHTFPAVLQSSGLY

SLSSVVTVPSSSLGTKTYTCNVDHKPSNTKVDKRVE

SKYGPPCPPCPAPEAAGGPSVFLFPPKPKDTLMISRTP

EVTCVVVDVSQEDPEVQFNWYVDGVEVHNAKTKP

REEQFNSTYRVVSVLTVLHQDWLNGKEYKCKVSNK

GLPSSIEKTISKAKGQPREPQVYTLPPSQEEMTKNQV

SLTCLVKGFYPSDIAVEWESNGQPENNYKTTPPVLD

SDGSFFLYSRLTVDKSRWQEGNVFSCSVMHEALHN

HYTQKSLSLSLG

An antibody having LC of SEQ ID NO: 6 (with $X_{aa}$ at residue 33 of SEQ ID NO: 6 being A) and HC of SEQ ID NO: 2 (hereinafter referred to as "mAb D"):

Light Chain
DIVMTQTPLSSPVTLGQPASISCRSSQSLVHRAGNTY

LSWLQQRPGQPPRLLIYKISNRFSGVPDRFSGSGAGT

DFTLKISRVEAEDVGVYYCMQARQFPLTFGGGTKVE

IKRTVAAPSVFIFPPSDEQLKSGTASVVCLLNNFYPRE

AKVQWKVDNALQSGNSQESVTEQDSKDSTYSLSST

LTLSKADYEKHKVYACEVTHQGLSSPVTKSFNRGEC

Heavy Chain
EVQLVESGGGLVKPGGSLRLSCAASGFTFSGVSINW

VRQAPGKGLEWVSSETTSSGTIYYADSVKGRFTISRD

NAKNSLYLQMNSLRAEDTAVYYCARSYYYGMDVW

GQGTTVTVSSASTKGPSVFPLAPSSKSTSGGTAALGC

LVKDYFPEPVTVSWNSGALTSGVHTFPAVLQSSGLY

SLSSVVTVPSSSLGTQTYICNVNHKPSNTKVDKRVEP

KSCDKTHTCPPCPAPEAEGAPSVFLFPPKPKDTLMIS

RTPEVTCVVVDVSHEDPEVKFNWYVDGVEVHNAKT

-continued
```
KPREEQYNSTYRVVSVLTVLHQDWLNGKEYKCKVS

NKALPSSIEKTISKAKGQPREPQVYTLPPSREEMTKN

QVSLTCLVKGFYPSDIAVEWESNGQPENNYKTTPPV

LDSDGSFFLYSKLTVDKSRWQQGNVFSCSVMHEAL

HNHYTQKSLSLSPGK
```

An antibody having LC of SEQ ID NO: 6 (with $X_{aa}$ at residue 33 of SEQ ID NO: 6 being Q) and HC of SEQ ID NO: 2 (hereinafter referred to as "mAb E"):

```
Light Chain
DIVMTQTPLSSPVTLGQPASISCRSSQSLVHRQGNTY

LSWLQQRPGQPPRLLIYKISNRFSGVPDRFSGSGAGT

DFTLKISRVEAEDVGVYYCMQARQFPLTFGGGTKVE

IKRTVAAPSVFIFPPSDEQLKSGTASVVCLLNNFYPRE

AKVQWKVDNALQSGNSQESVTEQDSKDSTYSLSST

LTLSKADYEKHKVYACEVTHQGLSSPVTKSFNRGEC

Heavy Chain
EVQLVESGGGLVKPGGSLRLSCAASGFTFSGVSINW

VRQAPGKGLEWVSSETTSSGTIYYADSVKGRFTISRD

NAKNSLYLQMNSLRAEDTAVYYCARSYYYGMDVW

GQGTTVTVSSASTKGPSVFPLAPSSKSTSGGTAALGC

LVKDYFPEPVTVSWNSGALTSGVHTFPAVLQSSGLY

SLSSVVTVPSSSLGTQTYICNVNHKPSNTKVDKRVEP

KSCDKTHTCPPCPAPEAEGAPSVFLFPPKPKDTLMIS

RTPEVTCVVVDVSHEDPEVKFNWYVDGVEVHNAKT

KPREEQYNSTYRVVSVLTVLHQDWLNGKEYKCKVS

NKALPSSIEKTISKAKGQPREPQVYTLPPSREEMTKN

QVSLTCLVKGFYPSDIAVEWESNGQPENNYKTTPPV

LDSDGSFFLYSKLTVDKSRWQQGNVFSCSVMHEAL

HNHYTQKSLSLSPGK
```

An antibody having LC of SEQ ID NO: 6 (with $X_{aa}$ at residue 33 of SEQ ID NO: 6 being N) and HC of SEQ ID NO: 2 (hereinafter referred to as "mAb F"):

```
Light Chain
DIVMTQTPLSSPVTLGQPASISCRSSQSLVHRNGNTY

LSWLQQRPGQPPRLLIYKISNRFSGVPDRFSGSGAGT

DFTLKISRVEAEDVGVYYCMQARQFPLTFGGGTKVE

IKRTVAAPSVFIFPPSDEQLKSGTASVVCLLNNFYPRE

AKVQWKVDNALQSGNSQESVTEQDSKDSTYSLSST

LTLSKADYEKHKVYACEVTHQGLSSPVTKSFNRGEC

Heavy Chain
EVQLVESGGGLVKPGGSLRLSCAASGFTFSGVSINW

VRQAPGKGLEWVSSETTSSGTIYYADSVKGRFTISRD

NAKNSLYLQMNSLRAEDTAVYYCARSYYYGMDVW
```

-continued
```
GQGTTVTVSSASTKGPSVFPLAPSSKSTSGGTAALGC

LVKDYFPEPVTVSWNSGALTSGVHTFPAVLQSSGLY

SLSSVVTVPSSSLGTQTYICNVNHKPSNTKVDKRVEP

KSCDKTHTCPPCPAPEAEGAPSVFLEPPKPKDTLMIS

RTPEVTCVVVDVSHEDPEVKFNWYVDGVEVHNAKT

KPREEQYNSTYRVVSVLTVLHQDWLNGKEYKCKVS

NKALPSSIEKTISKAKGQPREPQVYTLPPSREEMTKN

QVSLTCLVKGFYPSDIAVEWESNGQPENNYKTTPPV

LDSDGSFFLYSKLTVDKSRWQQGNVFSCSVMHEAL

HNHYTQKSLSLSPGK
```

Further, the present invention provides an antibody prepared according to a process, wherein said process comprises cultivating a host cell comprising a polynucleotide sequence of the present invention, under conditions such that the antibody is expressed, and recovering from said host cell an antibody of the present invention.

As used herein, an "antibody" is an immunoglobulin molecule comprising 2 HCs and 2 LCs interconnected by disulfide bonds. The amino terminal portion of each LC and HC includes a variable region of about 100-120 amino acids primarily responsible for antigen recognition via the CDRs contained therein. The CDRs are interspersed with regions that are more conserved, termed framework regions ("FR"). Each LCVR and HCVR is composed of 3 CDRs and 4 FRs, arranged from amino-terminus to carboxy-terminus in the following order: FR1, CDR1, FR2, CDR2, FR3, CDR3, FR4. The 3 CDRs of the LC are referred to as "LCDR1, LCDR2, and LCDR3," and the 3 CDRs of the HC are referred to as "HCDR1, HCDR2, and HCDR3." The CDRs contain most of the residues which form specific interactions with the antigen. The functional ability of an antibody to bind a particular antigen is largely influenced by the six CDRs. Assignment of amino acids to CDR domains within the LCVR and HCVR regions of the antibodies of the present invention is based on the well-known Kabat numbering convention (Kabat, et al., *Ann. NY Acad. Sci.* 190: 382-93 (1971); Kabat et al., *Sequences of Proteins of Immunological Interest*, Fifth Edition, U.S. Department of Health and Human Services, NIH Publication No. 91-3242 (1991)), and North numbering convention (North et al., *A New Clustering of Antibody CDR Loop Conformations*, Journal of Molecular Biology, 406:228-256 (2011)).

LCs are classified as kappa or lambda, which are each characterized by a particular constant region as known in the art. The antibodies of the present invention include kappa LCs. HCs are classified as gamma, mu, alpha, delta, or epsilon, and define the isotype of an antibody as IgG, IgM, IgA, IgD, or IgE, respectively. The antibodies of the present invention include IgG HCs. IgG antibodies can be further divided into subclasses, e.g., IgG1, IgG2, IgG3, IgG4. In a particular embodiment, the antibodies of the present invention are IgG4 or IgG1. The carboxy-terminal portion of each HC defines a constant region primarily responsible for effector function. In a particular embodiment, the antibodies of the present invention have one or more modifications in the constant region of each HC that reduces effector function or improves antibody stability.

The antibodies of the present invention are monoclonal antibodies ("mAbs"). mAbs can be produced, for example, by hybridoma technologies, recombinant technologies, phage display technologies, synthetic technologies, e.g., CDR-grafting, or combinations of such or other technologies known in the art. As referred to herein, mAbs are antibodies derived from a single copy or clone including, for example, any eukaryotic, prokaryotic or phage clone, and not the method by which it is produced.

Methods of producing and purifying antibodies are well known in the art. For example, a phage library can be screened, whereby thousands of Fab fragments are screened for interaction with recombinant human Trk. Resulting interactions can be recovered, purified, and the amino acid sequences determined using conventional methods well known in the art, whereby initial lead antibodies can be constructed. The antibodies of the present invention are engineered to contain one or more human framework regions. Human framework germline sequences can be obtained from ImMunoGeneTics (INGT) via their website, http://imgt.cines.fr, or from *The Immunoglobulin FactsBook* by Marie-Paule Lefranc and Gerard Lefranc, Academic Press, 2001, ISBN 012441351. According to particular embodiments, germline HC and LC framework regions for use in the antibodies of the present invention include 3-21 and A23, respectively.

In particular embodiments of the present invention, the antibody, or the nucleic acid encoding same, is provided in isolated form. As used herein, the term "isolated" refers to a protein, peptide, or nucleic acid which is free or substantially free from other macromolecular species found in a cellular environment.

The antibodies of the present invention may be prepared and purified using known methods. For example, cDNA sequences encoding a HC (for example the amino acid sequence given by SEQ ID NO: 1) and a LC (for example, the amino acid sequence given by SEQ ID NO: 6) may be cloned and engineered into a GS (glutamine synthetase) expression vector. The engineered immunoglobulin expression vector may then be stably transfected into CHO cells. As one of skill in the art will appreciate, mammalian expression of antibodies will result in glycosylation, typically at highly conserved N-glycosylation sites in the Fc region. Stable clones may be verified for expression of an antibody specifically binding TrkA. Positive clones may be expanded into serum-free culture medium for antibody production in bioreactors. Media, into which an antibody has been secreted, may be purified by conventional techniques. For example, the medium may be conveniently applied to a Protein A or G Sepharose FF column that has been equilibrated with a compatible buffer, such as phosphate buffered saline. The column is washed to remove nonspecific binding components. The bound antibody is eluted, for example, by pH gradient and antibody fractions are detected, such as by SDS-PAGE, and anti-TrkA vs. TrkA are pooled. The antibody may be concentrated and/or sterile filtered using common techniques. Soluble aggregate and multimers may be effectively removed by common techniques, including size exclusion, hydrophobic interaction, ion exchange, or hydroxyapatite chromatography. The product may be immediately frozen, for example at −70° C., or may be lyophilized.

The antibodies of the present invention can be used in the treatment of patients. More particularly the antibodies of the present invention are expected to treat a class of pain, such as acute or chronic pain of nociceptive/inflammatory, neuropathic, nociplastic, or mixed etiologies. Such pain expressly includes, but is not limited to, post-surgical pain, neuropathic pain, rheumatoid arthritis pain and osteoarthritis pain, including, for example, non radicular (non-neuropathic) and radicular CLBP, DNP, and LSR. Although antibodies of the present invention are expected to be useful in the treatment of pain, including post-surgical pain, neuropathic pain, rheumatoid arthritis pain and osteoarthritis pain as described above, such antibodies may also be useful in the treatment of other pain. As used interchangeably herein, "treatment" and/or "treating" and/or "treat" are intended to refer to all processes wherein there may be a slowing, interrupting, arresting, controlling, stopping, or reversing of the progression of the disorders described herein, but does not necessarily indicate a total elimination of all disorder symptoms. Treatment may also include the prevention of pain.

Treatment includes administration of an antibody of the present invention for treatment of a disease or condition in a human that would benefit from a reduction in TrkA activity, and includes: (a) inhibiting further progression of the disease, i.e., arresting its development; (b) relieving the disease, i.e., causing regression of the disease or disorder or alleviating symptoms or complications thereof; and (c) preventing the onset of the disease of symptoms.

Treatment, as defined herein, expressly includes reducing incidence of pain, ameliorating a pain or one or more symptoms of a pain, palliating a pain or one or more symptoms of a pain, delaying the development of pain. Treatment also includes, in some situations, treating the pain but not necessarily modifying the underlying disease or condition giving rise to the pain.

"Reducing incidence" of pain means any of reducing severity (which can include reducing need for and/or amount of (e.g., exposure to) other drugs and/or therapies generally used for this conditions, including, for example, opiates), duration, and/or frequency (including, for example, delaying or increasing time to post-surgical pain in an individual). As is understood by those skilled in the art, individuals may vary in terms of their response to treatment, and, as such, for example, a "method of reducing incidence of rheumatoid arthritis pain or osteoarthritis pain in an individual" reflects administering the antibody based on a reasonable expectation that such administration may likely cause such a reduction in incidence in that particular individual.

"Ameliorating" a pain or one or more symptoms of a pain (such as rheumatoid arthritis pain or osteoarthritis pain) means a lessening or improvement of one or more symptoms of a pain as compared to not administering an antibody. "Ameliorating" also includes shortening or reduction in duration of a symptom.

"Palliating" a pain or one or more symptoms of a pain (such as rheumatoid arthritis pain or osteoarthritis pain) means lessening the extent of one or more undesirable clinical manifestations of post-surgical pain in an individual or population of individuals treated with an antibody in accordance with the invention.

As used therein, "delaying" the development of pain means to defer, hinder, slow, retard, stabilize, and/or postpone progression of pain, such as post-surgical pain, rheumatoid arthritis pain, or osteoarthritis pain. This delay can be of varying lengths of time, depending on the history of the disease and/or individuals being treated. As is evident to one skilled in the art, a sufficient or significant delay can, in effect, encompass prevention, in that the individual does not develop pain. A method that "delays" development of the symptom is a method that reduces probability of developing the symptom in a given time frame and/or reduces extent of the symptoms in a given time frame, when compared to not using the method. Such comparisons are typically based on clinical studies, using a statistically significant number of subjects.

"Pain" as used herein refers to pain of any etiology including pain of nociceptive/inflammatory etiology, pain of neuropathic etiology, pain of nociplastic etiology, or pain of mixed etiologies. Pain expressly includes acute and chronic pain. Pain expressly includes acute or chronic pain that is musculoskeletal or neuropathic in origin. Pain also includes any pain with an inflammatory component. Pain also includes visceral pain (such as, for example, chronic prostatitis, interstitial cystitis (bladder pain) or chronic pelvic pain). Non-limiting eExamples of pain include post-surgical pain, post-operative pain (including dental pain), migraine, headache and trigeminal neuralgia, pain associated with burn, wound or kidney stone, pain associated with trauma (including traumatic head injury), neuropathic pain, pain associated with musculo-skeletal disorders such as rheumatoid arthritis, osteoarthritis, including, for example, non radicular (non-neuropathic) and radicular CLBP (including LSR or sciatici), DNP, ankylosing spondylitis, sero-negative (non-rheumatoid) arthropathies, non-articular rheumatism and peri-articular disorders, and pain associated with cancer (including "break-through pain" and pain associated with terminal cancer), peripheral neuropathy and post-herpetic neuralgia. Non-limiting examples of pain with an inflammatory component (in addition to some of those described above) include rheumatic pain, pain associated with mucositis, and dysmenorrhea.

Pain, as defined herein, expressly includes chronic pain of both musculoskeletal as well as neuropathic origin. Pain also expressly includes acute pain or sudden pain.

"Post-surgical pain" (interchangeably termed "post-incisional" or "post-traumatic pain") refers to pain arising or resulting from an external trauma such as a cut, puncture, incision, tear, or wound into tissue of an individual (including that that arises from all surgical procedures, whether invasive or non-invasive). As used herein, post-surgical pain does not include pain that occurs (arises or originates) without an external physical trauma. In some embodiments, post-surgical pain is internal or external (including peripheral) pain, and the wound, cut, trauma, tear or incision may occur accidentally (as with a traumatic wound) or deliberately (as with a surgical incision). As used herein, "pain" includes nociception and the sensation of pain, and pain can be assessed objectively and subjectively, using pain scores and other methods well-known in the art. Post-surgical pain, as used herein, includes allodynia (i.e., increased response to a normally non-noxious stimulus) and hyperalgesia (i.e., increased response to a normally noxious or unpleasant stimulus), which can in turn, be thermal or mechanical (tactile) in nature. In some embodiments, the pain is characterized by thermal sensitivity, mechanical sensitivity and/or resting pain. In some embodiments, the post-surgical pain comprises mechanically-induced pain or resting pain. In other embodiments, the post-surgical pain comprises resting pain. The pain can be primary or secondary pain, as is well-known in the art.

As used interchangeably herein, the term "patient," "subject," and "individual," refers to a human. In certain embodiments, the patient is further characterized with a disease, disorder, or condition (e.g., pain, for example primary or secondary headache and/or migraine including chronic migraine) that would benefit from a reduction in TrkA activity. In another embodiment, the patient is further characterized as being at risk of developing a condition described above, or condition that would benefit from a reduction in TrkA activity.

As used herein, the term "bind", "binds" or "binds to" refers to an interaction of an antibody with an epitope of human TrkA. The term "epitope" as used herein refers to discrete, three-dimensional sites of an antigen that are recognized by the antibodies of the present invention.

An antibody of the present invention can be incorporated into a pharmaceutical composition which can be prepared by methods well known in the art and comprise an antibody of the present invention and one or more pharmaceutically acceptable carrier(s) and/or diluent(s) (e.g., Remington, *The Science and Practice of Pharmacy*, 22$^{nd}$ Edition, Loyd V., Ed., Pharmaceutical Press, 2012, which provides a compendium of formulation techniques as are generally known to practitioners). Suitable carriers for pharmaceutical compositions include any material which, when combined with the antibody of the present invention, retains the molecule's activity and is non-reactive with the patient's immune system.

A pharmaceutical composition comprising an antibody of the present invention can be administered to a patient at risk for, or exhibiting, diseases or disorders as described herein by parental routes (e.g., subcutaneous, intravenous, intraperitoneal, intramuscular, or transdermal). A pharmaceutical composition of the present invention contains an "effective" or "therapeutically effective" amount, as used interchangeably herein, of an antibody of the present invention. An effective amount refers to an amount necessary (at dosages and for periods of time and for the means of administration) to achieve the desired therapeutic result. An effective amount of the antibody may vary according to factors such as the disease state, age, sex, and weight of the individual, and the ability of the antibody to elicit a desired response in the individual. An effective amount is also one in which any toxic or detrimental effects of the antibody of the present invention are outweighed by the therapeutically beneficial effects. An effective amount, in some embodiments, provides a clinically significant reduction in pain.

EXAMPLES

The Examples use some of the presently claimed antibodies, including mAb A, mAb B, mAb C, mAb D, and mAb E, wherein the sequences of such antibodies are given herein.

Example 1. Engineering, Expression, and Purification of mAbs A-E

To develop antibodies specific for TrkA, AlivaMab mice (Ablexis), transgenic for human immunoglobulin variable regions, are immunized with His-tagged Human TrkA extracellular domain (ECD). Mouse B cells positive for human TrkA binding are sorted by Fluorescence-activated cell sorting (FACS) and antibodies are cloned by single cell Polymerase Chain Reaction (PCR) as human IgG4PAA/Kappa antibodies. The engineered molecule is made as both an IgG4PAA isotype and an IgG1EN isotype.

The antibodies of the invention can be biosynthesized, purified, and formulated for administration by well-known methods. An appropriate host cell, such as Chinese hamster ovarian cells (CHO), is either transiently or stably transfected with an expression system for secreting antibodies using a predetermined HC:LC vector ratio if two vectors are used, or a single vector system encoding both heavy chain and light chain. Vectors suitable for expression and secretion of antibodies from these commonly-used host cells are well-known. Following expression and secretion of the antibody, the medium is clarified to remove cells. Clarified medium is applied to a Protein A affinity column that has been equilibrated with a compatible buffer, such as PBS (pH 7.4). The column is washed with buffer supplemented with 1M NaCl to remove nonspecific binding components. Bound antibody is eluted, for example, with sodium citrate at pH~3.5 and fractions are neutralized with 1M 2-amino-2-(hydroxymethyl)propane-1,3-diol (Tris) buffer. Antibody fractions are detected, such as by sodium dodecyl sulfate polyacrylamide gel electrophoresis (SDS-PAGE) or analytical size-exclusion, and then are pooled. Soluble aggregate and multimers may be effectively removed by common techniques, including size exclusion, hydrophobic interaction, ion exchange, or hydroxyapatite chromatography. An exemplified antibody of the present invention is concentrated and/or sterile filtered using common techniques. The purity of exemplified antibody after these chromatography steps is greater than 95% and samples may be immediately frozen at −70° C. or stored at 4° C. for several months.

The ability of the present Example antibodies to bind to and or inhibit signalling by TrkA can be assessed according to Examples 2-7.

Example 2. Binding Kinetics and Affinity of mAbs A-E

The binding kinetics and affinity of exemplified antibodies to human, cynomolgus monkey, rat, mouse, and rabbit TrkA are determined as described below using a surface plasmon resonance assay on a BIACORE™ 8K instrument (GE Healthcare). Two different isoforms of human TrkA (isoform 1 and isoform 2) are evaluated along with human TrkB and human TrkC. The BIACORE™ 8K is primed with HBS-EP+ running buffer [10 mM 2-[4-(2-hydroxyethyl)piperazin-1-yl]ethanesulfonic acid (Hepes pH 7.4, 150 mM NaCl, 3 mM ethylenediaminetetraacetic acid (EDTA), 0.05% polysorbate 20 surfactant (P20, TWEEN® 20)]. The analysis temperature is set at 37° C. and the sample compartment is set at 15° C. Binding kinetics and affinities are obtained using a parallel kinetics assay with an antibody capture method. Antibodies are captured onto a Series-S Sensor Protein A CM5 chip (GE Healthcare). For each channel, Flow Cell 1 (FC1) is designated as a buffer reference and Flow Cell 2 (FC2) is designated for antibody capture. All FC2 on all eight channels are set to capture approximately 89 response units (RU) of antibody at a flow rate of 10 µL/min. The antibody sample is prepared at 1 µg/mL by dilution into the running buffer. The human TrkA isoform 1 and 2, mouse, rat, rabbit and cynomolgus monkey TrkA analytes are prepared at a final concentration of 400, 200, 100, 50, 25, 12.5, 6.25, and 3.125 nM by dilution into the running buffer. The human TrkB and TrkC analytes are prepared at a final concentration of 800, 400, 200, 100, 50, 25, 12.5, and 6.25 nM by dilution into the running buffer. Before the analysis cycle, the chip is regenerated with 3 injections of glycine (pH~1.5) at 100 µL/min for a contact time of 15 seconds on FC1 and FC2 in order to clean the surface of the chip. Regeneration is followed by a conditioning step consisting of (1) 5 µg/mL of an IgG4 isotype control antibody at 5 µL/min for 15 seconds on FC2; (2) running buffer at 30 µL/min for 250 seconds and dissociation for 600 seconds on FC1 and FC2; (3) chip surface regeneration with an injection of glycine (pH~1.5) at 100 µL/min for a contact time of 15 seconds. Each analysis cycle consists of: (1) capturing the test antibody on all eight FC2, where all eight respective FC1 pairs are used as a buffer reference, at 10 µL/min; (2) running buffer wash step; (3) injection of TrkA, TrkB, or TrkC, at 100 µL/min for a contact time of 120 seconds on channels 1-8 in order of descending concentration; (4) return to buffer flow for a dissociation time of 600 seconds; (5) regeneration of the chip surface with two injections of glycine (pH~1.5), at 100 µL/min for 15 seconds per injection; (6) final running buffer wash step. Data is processed using predefined antibody parallel kinetics with reference subtraction and fit to a 1:1 binding model using BIACORE™ 8K evaluation software (version 1.1.1.7442) to determine the association rate (on-rate, kon, $M^{-1}s^{-1}$ units) and the dissociation rate (off-rate, koff, $s^{-1}$ units). The equilibrium dissociation constant ($K_D$) is calculated from the relationship $K_D = k_{off}/k_{on}$, in molar units. The average (Avg) $K_D$ and error, reported as the standard deviation (SD), is determined from three independent experiments unless noted otherwise. Exemplified antibodies demonstrate concentration-dependent binding to human, cynomolgus monkey, rat, mouse, and rabbit TrkA. At the highest concentration of human TrkB and human TrkC injected (800 nM), the binding response signal does not reach the theoretical half-maximal response signal. As a result, the $K_D$ of tested antibodies to human TrkB and human TrkC is estimated to be >800 nM. The results are shown in Table 1.

TABLE 1

BIACORE™ binding kinetics and affinity of mAbs A-E

| Antibody | Analyte | $k_{on}$ (1/Ms) Avg ± SD | $k_{off}$ (1/s) Avg ± SD | $K_D$ (nM) Avg ± SD | # Replicates |
|---|---|---|---|---|---|
| mAb A | Human TrkA Isoform 2 | 1.8 ± 0.1 E5 | 7.2 ± 0.03 E−4 | 4.1 ± 0.2 | 3 |
| | Human TrkA Isoform 1 | 1.8 ± 0.2 E5 | 6.9 ± 0.1 E−4 | 3.9 ± 0.5 | 3 |
| | Human TrkB | $K_D$ >800 nM | | | 3 |
| | Human TrkC | $K_D$ >800 nM | | | 3 |
| | Mouse TrkA | 1.1 ± 0.1 E5 | 6.9 ± 0.2 E−4 | 6.1 ± 0.5 | 3 |
| | Rat TrkA | 1.4 ± 0.1 E5 | 6.9 ± 0.2 E−4 | 5.1 ± 0.5 | 3 |
| | Cynomolgus monkey TrkA | 1.9 ± 0.1 E5 | 6.9 ± 0.04 E−4 | 3.6 ± 0.2 | 3 |
| | Rabbit TrkA | 2.1 ± 0.1 E5 | 6.1 ± 0.1 E−4 | 2.9 ± 0.2 | 3 |
| mAb B | Human TrkA Isoform 2 | 1.9 ± 0.1 E5 | 1.3 ± 0.01 E−3 | 6.8 ± 0.5 | 3 |
| | Human TrkA Isoform 1 | 1.9 ± 0.3 E5 | 1.3 ± 0.01 E−3 | 6.7 ± 0.9 | 3 |
| | Human TrkB | $K_D$ >800 nM | | | 3 |
| | Human TrkC | $K_D$ >800 nM | | | 3 |
| | Mouse TrkA | 1.2 ± 0.1 E5 | 1.2 ± 0.04 E−3 | 10.5 ± 0.7 | 3 |
| | Rat TrkA | 1.3 ± 0.1 E5 | 1.2 ± 0.05 E−3 | 9.1 ± 1.0 | 3 |
| | Cynomolgus monkey TrkA | 1.9 ± 0.2 E5 | 1.3 ± 0.02 E−3 | 6.9 ± 0.8 | 3 |
| | Rabbit TrkA | 2.2 ± 0.1 E5 | 1.1 ± 0.05 E−3 | 5.0 ± 0.3 | 3 |
| mAb C | Human TrkA Isoform 2 | 2.0 ± 0.1 E5 | 1.3 ± 0.04 E−3 | 6.6 ± 0.4 | 3 |
| | Human TrkA Isoform 1 | 2.0 ± 0.1 E5 | 1.3 ± 0.06 E−3 | 6.7 ± 0.6 | 3 |

TABLE 1-continued

BIACORE ™ binding kinetics and affinity of mAbs A-E

| Antibody | Analyte | $k_{on}$ (1/Ms) Avg ± SD | $k_{off}$ (1/s) Avg ± SD | $K_D$ (nM) Avg ± SD | # Replicates |
|---|---|---|---|---|---|
| | Human TrkB | | $K_D$ >800 nM | | 3 |
| | Human TrkC | | $K_D$ >800 nM | | 3 |
| | Mouse TrkA | 1.2 ± 0.4 E5 | 1.2 ± 0.04 E-3 | 10.2 ± 0.5 | 3 |
| | Rat TrkA | 1.3 ± 0.1 E5 | 1.2 ± 0.04 E-3 | 9.0 ± 0.2 | 3 |
| | Cynomolgus monkey TrkA | 2.0 ± 0.2 E5 | 1.3 ± 0.03 E-3 | 6.6 ± 0.6 | 3 |
| | Rabbit TrkA | 2.2 ± 0.1 E5 | 1.1 ± 0.1 E-3 | 4.7 ± 0.4 | 3 |
| mAb D | Human TrkA Isoform 2 | 2.5 E+05 | 1.3 E-03 | 4.9 | 1 |
| | Human TrkA Isoform 1 | 2.8 E+05 | 1.2E-03 | 4.4 | 1 |
| mAb E | Human TrkA Isoform 2 | 2.6 E+05 | 1.4E-03 | 5.2 | 1 |
| | Human TrkA Isoform 1 | 2.7 E+05 | 1.3E-03 | 4.8 | 1 |

The sequences of the Trk proteins listed in the "Analyte" column in Table 1 are given below in SEQ ID NOs: 20-27.

Example 3. In Vitro Neurite Outgrowth Assay of mAbs A-E

Inhibition of NGF induced neurite outgrowth on neurons is assessed using rat NEUROSCREEN™-1 cells (pheochromocytoma PC12 subclone, CELLOMICS®). The cells are maintained in F-12K basal medium, 12.5% heat inactivated horse serum, 2.5% heat inactivated fetal bovine serum (FBS), 1× GlutaMAX™ (INVITROGEN™, Cat. #35050061), and 1× Anti-Anti (INVITROGEN™, Cat. #15240) at 37° C., 95% humidity, in collagen coated flasks. To measure neurite outgrowth, the NEUROSCREEN™-1 cells are seeded into Collagen I 96-well plates at 2000 cells per well in growth medium using only the interior 60 wells. On the following day, the medium is removed and replaced with fresh growth medium containing an 8 point dilution series of anti-TrkA antibodies in the presence or absence of NGF (R&D SYSTEMS®, Cat #:256-GF) at 25 ng/mL. There are three technical replicates for each point in the dilution series. The plates are incubated for 4 days at 37° C., 95% humidity, and then fixed with 1× Prefer fixative (Anatech, Ltd) for 1 hour. The plates are washed twice with 1× Dulbecco's Phosphate-Buffered Saline (DPBS) and once with 1× NO buffer [1×DBPS, 0.5% bovine serum albumin (BSA), 0.01% saponin]. The cells are immuno-stained overnight with primary antibody mouse anti-beta 3 tubulin (TU-20, INVITROGEN™, Cat. # MA1-19187) diluted 1:800 in NO buffer and for >2 hours with secondary antibody goat anti-mouse DYLIGHT® 488 (INVITROGEN™, Cat. #35502) diluted 1:500 in NO buffer. The plates are washed once with NO buffer, twice with DPBS, sealed, and loaded onto the CELLINSIGHT™ Instrument for high content imaging and analysis using the Neuronal Profiling v4.0 algorithm. Data generated by the algorithm is processed for $IC_{50}$ calculation with GraphPad PRISM® software. The results are shown in Table 2.

TABLE 2

In vitro Neurite Outgrowth Activity

| Antibody | IC50 (nM) | % Max Stimulation |
|---|---|---|
| mAb A | 0.10 | 7 |
| mAb B | 0.07 | 10 |
| mAb C | 0.06 | 7 |
| mAb D | 0.08 | 17 |
| mAb E | 0.07 | 17 |

Exemplified anti-TrkA antibodies show concentration-dependent inhibition of NGF-induced neurite outgrowth. Exemplified antibodies D and E showed consistently greater stimulatory effects on neurite outgrowth in the absence of NGF.

Example 4. Inhibition of NGF-Induced Phosphorylation of Human or Rat TrkA of mAbs A-E (and Some Comparative Data)

Inhibition of rat or human NGF-stimulated phosphorylation of TrkA is assessed in cells that were transfected and express either the rat or human TrkA receptor in human embryonic kidney cells (HEK293) or standard fibroblast cells (3T3) background, respectively. Cells are incubated with PBS or test antibody for 5 minutes prior to a 5 minute stimulation with or without 10 µg/mL rat or human β-NGF at room temperature. Antibody concentrations range from 1 µM to 0.1 pM in a volume of 300-450 µL PBS (Gibco, Cat #20012-027) in 1.5 mL Eppendorf tubes. Samples are frozen on dry ice and stored at −80° C. until extraction. Cell Lysis buffer consists of 2× Tissue Lysis buffer (CELL SIGNALLING TECHNOLOGY®, Cat. #9803S), with 100×HALT™ protease and phosphatase inhibitor cocktail (ThermoFisher) and 1 mM phenylmethylsulfonyl fluoride. Lysis buffer is added to each tube and homogenized (Qiagen Homogenizer) for 10 seconds on ice. Supernatants resulting from centrifugation at 4° C. for 15 minutes at 12,000 relative centrifugal force (RCF) are analyzed by ELISA methods to measure pTrkA, using methods described in Price et al (J Neurosci Methods 282:34-42, 2017), each sample measured in duplicate or quadruplicate.

Either the rat TrkA capture antibody (R&D SYSTEMS®, Cat. # AF1056) or the human TrkA capture antibody (R&D SYSTEMS®, Cat. # MAB1751) is diluted carbonate-bicarbonate buffer (PIERCE™ CHEMICAL, Cat. #28382) to 3 µg/mL and 100 µL per well is used to coat Black MAX-ISORP™ 96 well plates (NUNC™, Cat. #446471) overnight at 4° C. Plates are washed with 20 mM Tris-buffer saline containing 150 mM NaCl, pH~7.4 (TBS), blocked with 3% BSA (Sigma, Cat. # A3059) in TBS for 1 hour at room temperature, then blotted dry, sealed and stored at 4° C. before using within 2 weeks. Homogenates described above (100 µL) are added to each well and incubated at 4° C. overnight. Plates are washed with TBST (TBS with 0.05% TWEEN®-20, 3×300 µL/well) and the rabbit Phospho-TrkA (Tyr674/675)/TrkB (Tyr706/707) (CELL SIGNALLING TECHNOLOGY®, Cat. #4621) diluted 1:20,000 in 1% BSA/TBST, 100 µL per well added, and incubated for 2 hours at room temperature. Plates are washed as before and a secondary antibody, goat anti-rabbit alkaline phosphatase (Jackson Immunoresearch Labs, Cat. #111-055-144) is diluted 1:20,000 in 1% BSA/TBST, 100 µL per well added, and incubated for 1 hour at room temperature. Plates are washed 5×300 µL/well with TBST and 100 µL per well of alkaline phosphatase CDP-star substrate (APPLIED BIO- SYSTEMS™, Cat. # T2214) is added. Plates are read 30 minutes later in an Envision® (PerkinElmer) plate reader with an enhanced luminescent protocol. Resulting counts per second (CPS) are converted to percent of NGF signal with the equation: 100*(CPS sample−CPS control)/(CPS NGF−CPS control), plotted versus the concentration of exemplified antibodies, and a four parameter curve fit is determined using Graph Pad PRISM® 7 to give the $IC_{50}$/$EC_{50}$ values.

TABLE 3

Inhibition of NGF-induced phosphorylation of human TrkA

|  | mAb A | mAb D | mAb E | mAb C | mAb B |
|---|---|---|---|---|---|
|  | Counts per second (x 1000) | | | | |
| PBS | 160.2 | 346.0 | 149.9 | 162.8 | 216.7 |
| 10 µg/mL NGF | 1727.0 | 2937.7 | 1462.2 | 1639.1 | 2862.2 |
| +1 µM mAb | 341.3 | 971.2 | 629.8 | 394.5 | 438.5 |
| +100 nM mAb | 390.3 | 1444.1 | 739.0 | 511.3 | 446.1 |
| +10 nM mAb | 570.8 | 1204.5 | 799.5 | 620.1 | 717.4 |
| +1 nM mAb | 790.6 | 1348.6 | 837.9 | 1088.4 | 1072.1 |
| +100 pM mAb | 1207.6 | 2011.9 | 2777.7 | 2342.0 | 3969.5 |
| +10 pM mAb | 1540.7 | 2685.0 | 2756.0 | 2400.2 | 3436.8 |
| +1 pM mAb | 1442.3 | 2787.1 | 2194.4 | 1918.5 | 4337.0 |
| +0.1 pM mAb | 1195.6 | 2557.8 | 1853.3 | 2265.3 |  |
|  | IC50 and maximal inhibition from curve fits | | | | |
| IC50 (nM) | 0.77 | 0.12 | 0.48 | 0.80 | 0.58 |
| % Max Inhibition | 86% | 66% | 57% | 77% | 88% |

TABLE 4

Inhibition of NGF-induced phosphorylation of rat TrkA

|  | mAb A | mAb D | mAb E | mAb C | mAb B |
|---|---|---|---|---|---|
|  | Counts per second (x 1000) | | | | |
| PBS | 220.4 | 472.6 | 504.7 | 605.0 | 591.8 |
| 10 µg/mL NGF | 2129.7 | 3254.4 | 2760.0 | 2812.1 | 4292.6 |
| +1 µM mAb | 580.5 | 1932.3 | 1878.6 | 1296.5 | 2990.3 |
| +100 nM mAb | 544.4 | 2589.5 | 1699.3 | 1583.0 | 2337.2 |
| +10 nM mAb | 709.8 | 2429.8 | 2232.2 | 1529.4 | 2865.2 |
| +1 nM mAb | 1147.9 | 3158.7 | 2267.4 | 2669.0 | 3299.7 |
| +100 pM mAb | 1685.4 | 3792.3 | 3701.4 | 2946.6 | 5162.9 |
| +10 pM mAb | 2201.1 | 4515.5 | 3444.4 | 3680.1 | 4456.1 |
| +1 pM mAb | 2091.6 | 4056.7 | 3379.5 | 3050.8 | 4862.9 |
| +0.1 pM mAb | 1826.8 | 4533.3 | 2939.4 | 3377.0 | 4786.9 |
|  | IC50 and maximal inhibition from curve fits | | | | |
| IC50 (nM) | 0.57 | 0.68 | 0.68 | 1.6 | 0.72 |
| % Max Inhibition | 82% | 40% | 37% | 65% | 42% |

TABLE 5

Stimulation of human TrkA phosphorylation

|  | mAb A | mAb D | mAb E | mAb C | mAb B |
|---|---|---|---|---|---|
|  | Counts per second (x 1000) | | | | |
| PBS | 160.2 | 346.0 | 149.9 | 162.8 | 216.7 |
| 10 µg/mL NGF | 1727.0 | 2937.7 | 1462.2 | 1639.1 | 2862.2 |
| 1 µM mAb | 348.6 | 1022.2 | 482.8 | 420.5 | 366.6 |
| 100 nM mAb | 385.1 | 993.5 | 605.3 | 522.4 | 486.8 |
| 10 nM mAb | 472.9 | 1156.7 | 599.8 | 533.5 | 542.1 |
| 1 nM mAb | 404.0 | 935.1 | 487.3 | 513.4 | 313.1 |
| 100 pM mAb | 205.0 | 486.5 | 263.7 | 388.8 | 777.1 |
| 10 pM mAb | 160.8 | 334.7 | 194.2 | 286.4 | 560.7 |
| 1 pM mAb | 156.2 | 397.9 | 180.7 | 251.3 | 558.7 |
| 0.1 pM mAb | 131.5 | 277.3 | 177.7 | 242.2 | 433.4 |

TABLE 5-continued

Stimulation of human TrkA phosphorylation

|  | mAb A | mAb D | mAb E | mAb C | mAb B |
|---|---|---|---|---|---|
|  | EC50 and maximal stimulation from curve fits | | | | |
| EC50 (nM) | 0.13 | 0.28 | 0.29 | 0.075 | >1 µM |
| % Max stimulation | 15% | 27% | 31% | 23% |  |

TABLE 6

Stimulation of rat TrkA phosphorylation

|  | mAb A | mAb D | mAb E | mAb C | mAb B |
|---|---|---|---|---|---|
|  | Counts per second (x 1000) | | | | |
| PBS | 220.4 | 472.6 | 504.7 | 605.0 | 591.8 |
| 10 µg/mL NGF | 2129.7 | 3254.4 | 2760.0 | 2812.1 | 4292.6 |
| 1 µM mAb | 492.8 | 2051.7 | 2053.4 | 1626.6 | 1860.4 |
| 100 nM mAb | 572.5 | 2847.6 | 2018.1 | 1765.1 | 2075.5 |
| 10 nM mAb | 640.4 | 2967.3 | 2456.6 | 1690.2 | 2101.3 |
| 1 nM mAb | 442.0 | 2387.2 | 1818.5 | 1544.4 | 1396.1 |
| 100 pM mAb | 203.3 | 1248.4 | 1014.6 | 922.3 | 757.8 |
| 10 pM mAb | 226.9 | 626.9 | 609.5 | 663.8 | 637.9 |
| 1 pM mAb | 173.6 | 585.2 | 636.3 | 613.0 | 844.0 |
| 0.1 pM mAb | 171.3 | 570.8 | 738.8 | 570.7 | 747.7 |
|  | EC50 and maximal Stimulation from curve fits | | | | |
| EC50 (nM) | 0.88 | 0.17 | 0.30 | 0.21 | 0.98 |
| % Max stimulation | 18% | 77% | 74% | 50% | 38% |

Exemplified anti-TrkA antibodies show concentration-dependent inhibition of NGF-induced phosphorylation of rat and human TrkA receptors. The exemplified mAb B was tested in two other independent experiments and the complete set of experiments summarized in table 7. The proported TrkA receptor antibodies mAb 1 and mAb 2 failed in inhibit (IC50>1000 nM) NGF-induced phosphorylation of human TrkA receptors. (mAb 1 and mAb 2 were made and purified as outlined below.)

TABLE 7

Stimulation or inhibition of NGF-induced phosphorylation of rat or human TrkA.

|  | Human pTrkA | | | |
|---|---|---|---|---|
|  | EC50 (nM) | % Stim.* | IC50 (nM) | % Inh.* |
| mAb A | 0.13 | 15% | 0.77 | 86% |
| mAb B | ND#, 0.46, 0.35 | <15%, 18%, 36% | 0.58, 0.84, 1.07 | 88%, 77%, 74% |
| mAb C | 0.075 | 23% | 0.80 | 77% |
| mAb D | 0.28 | 27% | 0.12 | 66% |
| mAb E | 0.29 | 31% | 0.48 | 56% |
| mAb 1 | <1000 |  | <1000 |  |
| mAb 2 | <1000 |  | <1000 |  |

*Maximal stimulation or inhibition from the curve fit as a percent of the NGF-stimulated response
ND = Not Determined as the simulation signal was too low to allow an accurate curve fit.

Example 5. TrkA Receptor Antibody Internalization In Vitro of mAb A

Fluorescence signal corresponding to total and internalization of mAb A is measured by performing high content live cell imaging assay in four different cell lines (human TrkA 3T3, SKNSH neuroblastoma, rat TrkA HEK293, and PC12 pheochromocytoma). Briefly, 33 nM (5 µg/mL) of mAb A is mixed with 0.2 µM (10 µg/mL) of anti-human IgG Fcγ fragment specific Fab fragment (Jackson ImmunoResearch, Cat. #109-007-008) labelled with either DYLIGHT® 650 (Thermo Fisher, Cat. #62266) or pHAb dye (Promega, Cat. # G9845) in culture media and incubated overnight with live cells grown in a 96 well plate at 37° C. The following day, the cells are washed, incubated for 20 min with NUCBLUE® Hoechst dye (Thermo Fisher, Cat. # R37605), washed again, and imaged with CYTATION™ 5 High Content Imager) (BIOTEK®). DYLIGHT® 650 signal measures total antibody levels while pHAb pH sensor dye signal measures only internalized fluorescence. The intensity of the signal in each well is divided by the number of Hoechst stained nuclei to determine signal intensity per cell. The background signal is determined from human IgG isotype control and subtracted from the final value. The internalized fluorescence signal is then normalized to total antibody fluorescence by DYLIGHT®650 to determine relative fluorescence across cell lines.

TABLE 7A

Internalization of TrkA receptor antibody mAb A

| mAb A background subtracted fluorescence per cell, normalized to total antibody levels | Total | Internalized |
| --- | --- | --- |
| hTrkA 3T3 (mean ± SD, N = 2) | 100.00% | 33.42 ± 1.15% |
| SKNSH (mean ± SD, N = 2) | 100.00% | 42.64 ± 27.79% |
| rTrkA HEK293 (mean ± SD, N = 2) | 100.00% | 52.62 ± 5.12% |
| PC12 (mean ± SD, N = 2) | 100.00% | 66.65 ± 11.08% |

Example 6. Attenuation of CFA-Induced Gait Deficit In Vivo of mAb A

Attenuation of temporal and spatial gait features induced by Complete Freund's Adjuvant (CFA) delivered to the intra-articular space is assessed with the mAb A of the present invention as previously described (Adams, et al., 2016). Briefly, female Sprague Dawley rats (Envigo) weighing between 175 and 209 g at the start of testing are group-housed with access to food and water ad libitum except during testing. Rats receive a habituation session to the ExerGait treadmill apparatus (Columbus Instruments) at the start of the study. A digital camera (Basler) records activity at 100 frames/second while rats walk on the treadmill belt, approximately 10.5" long×3.5" wide, housed within a plexiglass chamber. During the habituation session, the rats are placed into the chamber for approximately 30 seconds with the treadmill turned off. The treadmill is turned on and slowly increased incrementally to 3 cm/sec, 8 cm/sec, 12 cm/sec, and 15 cm/sec while the rat makes two attempts to walk forward. Following habituation, rats receive a 50 µL intra-articular injection of Complete Freund's Adjuvant (1 mg/mL concentration CFA, Sigma lot #: SLBK1731V) mixed with Freund's Incomplete Adjuvant (IFA, MP Biomedicals LLC, Cat. #:642861, lot #:07263) to form a 0.4 mg/L (1 mL/kg) of 10 mg/kg IgG4 negative control, 0.1, 1, or 10 mg/kg of mAb A, or a positive control. mAb A (lot number BE05366-048) is diluted from the initial concentration of 12.4 mg/mL to 0.1, 1 and 10 mg/mL in PBS. The control IgG4PAA is diluted from 14.5 mg/mL to 10 mg/mL in PBS. Test sessions are conducted at 1, 2, and 3 days post-CFA administration. For each test session, rats are placed into the chamber and the treadmill is slowly ramped from 0 cm/sec to 16 cm/sec. Video is recorded at 16 cm/sec of the rats walking over a sufficient number of frames (approximately 1200-2000 frames). The dependent measures include: range of motion for each limb (subtraction of distance from the rear paw to the body midline at the beginning of the stance to the end of the stance), stance/swing ratio (stance time divided by the swing time for each limb), normalized stance distance (multiplication of percent of time in the stride in the stance phase by the total stride length), and the paw print size (number of pixels detected in the paw print as determined by pre-set color conditions that capture the limb in contact with the treadmill). These four endpoints are transformed to index measures by comparison to the contralateral limb which is not injected with CFA in order to provide a percentage of change from the control limb. All four measures are then summed to provide the Gait Index Score. Repeated measures ANOVAs are conducted with an alpha level of 0.05, followed by Dunnet's post-hoc comparisons to the IgG4 control. The 1 mg/kg and 10 mg/kg dose levels of mAb A both showed statistically significant improvement in composite Gait Index Score vs. IgG4 controls (as indicated by the * in the table).

TABLE 8

Effects of mAb A on CFA-induced Gait Deficits Three Days Post-Dosing

| Antibody | Range of Motion | Stance/Swing Ratio | Normalized Stance Distance | Paw Print Size | Composite Gait Score |
| --- | --- | --- | --- | --- | --- |
| IgG4 Control | −74.36 | −75.43 | −59.18 | −54.95 | −263.92 ± 6.62 |
| 0.1 mg/kg mAb A | −46.18 | −63.87 | −37.44 | −38.47 | −185.96 ± 26.15 |
| 1 mg/kg mAb A | −22.72 | −41.31 | −20.17 | −20.11 | −104.3 ± 24.93* |
| 10 mg/kg mAb A | −26.58 | −43.6 | −25.51 | −22.9 | −118.59 ± 23.08* |

N = 9-10/group, mean ± SEM,
* = p < 0.05

Example 7. Inhibition of NGF-Induced Phosphorylation of TrkA Ex Vivo in Brain, Skin and Dorsal Root Ganglia of mAb A Inhibition of NGF stimulated phosphorylation of TrkA is assessed ex vivo in brain skin or dorsal root ganglia tissue. Female Sprague Dawley rats are euthanized and one hippocampus combined with one caudate brain area per 2 mL Eppendorf tubes containing either 100 µL PBS (Gibco, Cat. #20012-027) or 100 µL rat β-NGF (10 µg/mL in PBS). Similarly, two 6 mm skin punches are taken from hind paw pad and placed in a 2 mL tube containing 150 µL PBS or 150 µL rat β-NGF (Sigma-Aldrich, Cat. # N-2513, 10 µg/mL in PBS). Dorsal root ganglia are dissected and 10 ganglia placed in a 2 mL tube containing 200 µL PBS or 150 µL rat β-NGF (10 µg/mL in PBS). Two 5 mm stainless steel beads are added to each sample and shaken by hand for 10 seconds and incubated at room temperature for 5 minutes. Samples are frozen on dry ice and stored at −80° C. until extraction. Cell lysis buffer consisting of 2× Tissue Lysis buffer (CELL SIGNALING TECHNOLOGY®, Cat. #9803S), 1×HALT™ protease, phosphatase inhibitor cocktail (ThermoFisher, Cat #78441) and 1 mM phenylmethanesulfonyl fluoride is added to each tube (to give a total volume of 500 µL) and homogenized using a Qiagen tissuelyzer set at 30 Hz 2×3 minutes. Supernatants resulting from centrifugation at 4° C. for 15 minutes at 12,000 RCF are analyzed by ELISA methods to measure pTrkA, using procedures described in Price et al. (J Neurosci Methods 282:34-42, 2017).

Either the rat TrkA capture antibody (R&D SYSTEMS®, Cat. # AF1056) or the human TrkA capture antibody (R&D SYSTEMS®, Cat. # MAB1751) is diluted in carbonate-bicarbonate buffer (THERMO SCIENTIFIC™ PIERCE™ CHEMICAL, Cat. #28382) to 3 µg/mL and 100 µL per well used to coat Black MAXISORP® 96 well plates (NUNC™, Cat. #446471) overnight at 4° C. Plates are washed with 20 mM Tris-buffer saline (INVITROGEN™, Cat. #15567-027) containing 150 mM NaCl NaCl (Sigma-Aldrich, Cat. # S3014-500G), pH 7.4 (TBS), blocked with 3% BSA (Sigma-Aldrich, Cat. # A3059) in TBS for 1 hour at room temperature, blotted dry, sealed, and stored at 4° C. before using within 2 weeks. Homogenates described above (100 µL) are added to each well and incubated at 4° C. overnight. Plates are washed with TBST (TBS with 0.05% TWEEN®-20 (Fisher Biochemical, Cat. # BP337100), 3×300 µL/well) and the rabbit phospho-TrkA (Tyr674/675)/TrkB (Tyr706/707) (CELL SIGNALING TECHNOLOGY®, Cat. #4621) is diluted 1:20,000 in 1% BSA/TBST, 100 µL per well is added and plates are incubated for 2 hours at room temperature on a gentle shaker. Plates are washed as before and a secondary antibody, goat anti-rabbit alkaline phosphatase (Jackson Immunoresearch Laboratories, INC., Cat. #111-055-144) diluted 1:20,000 in 1% BSA/TBST, is added (100 µL per well) and incubated for 1 hour at room temperature. Plates are washed 5×300 µL/well with TBST, and 100 µL per well of alkaline phosphatase CDP-star substrate (APPLIED BIOSYSTEMS™, Cat. # T2214) is added. Plates are read 30 minutes later on an ENVISION® (PerkinElmer) plate reader with an enhanced luminescent protocol. Resulting mean counts per second (CPS) for baseline and NGF stimulated for each tissue sample from each animal are presented in table 9.

TABLE 9

Inhibiton of tissue TrkA

|  | IgG4 Control 10 mg/kg, SC | mAb A 0.1 mg/kg, SC | mAb A 1 mg/kg, SC | mAb A 10 mg/kg, SC |
|---|---|---|---|---|
| Counts per seconds (x1000) | | | | |
| Brain: | | | | |
| Baseline | 70.6 ± 12.8 (10) | 58.5 ± 5.3 (9) | 80.8 ± 14.2 (9) | 119.6 ± 25.5 (10) |
| NGF Stimulated | 506.6 ± 94.8 (10) | 383.4 ± 81.1 (9) | 476.6 ± 151.4 (9) | 327.0 ± 86.2 (10) |
| DRG: | | | | |
| Baseline | 109.0 ± 7.3 (5) | 99.8 ± 4.0 (5) | 110.5 ± 5.9 (5) | 109.7 ± 8.6 (5) |
| NGF Stimulated | 482.8 ± 60.4 (5) | 329.4 ± 46.4 (5)* | 226.9 ± 57.4 (5)** | 195.7 ± 28.2 (5)** |
| Skin: | | | | |
| Baseline | 14.5 ± 1.0 (9) | 15.9 ± 1.4 (9) | 16.2 ± 1.3 (9) | 16.0 ± 1.3 (9) |
| NGF Stimulated | 33.3 ± 2.6 (9) | 26.6 ± 2.6 (9)* | 22.3 ± 1.6 (9)** | 20.5 ± 1.4 (9)** |

Mean ± SEM (N)
*/**p < 0.05/0.001 vs NGF-stimulated IgG control, Two-way ANOVA followed by Dunnett's post hoc comparison.

The corresponding DNA sequences for the antibodies described herein may be prepared. Such DNA sequences for mAb A, mAb B, mAb C, mAb D, and mAb E are listed herein as indicated in the following table 10.

TABLE 10

Listing of DNA sequences for Some of the Antibodies Described Herein

| Antibody | DNA Light Chain | DNA Heavy Chain |
|---|---|---|
| mAb A | SEQ ID NO: 12 | SEQ ID NO: 13 |
| mAb B | SEQ ID NO: 14 | SEQ ID NO: 15 |
| mAb C | SEQ ID NO: 16 | SEQ ID NO: 15 |
| mAb D | SEQ ID NO: 17 | SEQ ID NO: 19 |
| mAb E | SEQ ID NO: 18 | SEQ ID NO: 19 |

Example 8. Blocking the Binding of Human Trk A to NGF of mAbs A-E

Each row of a 96-well high-binding clear-bottom microtiter plate (Microlon, #655061) was coated overnight at 4° C. with 100 µL/well of recombinant human TrkA protein, diluted to 2 µg/mL in phosphate buffered saline, pH 7.2 (PBS). The next day, the coating solution was removed, and the plate was blocked with 150 µL of Casein-PBS (Thermo Scientific, #37528) for 1 hour at 25° C. with gentle shaking. The plate was then washed three times with PBS supplemented with 0.05% Tween20 (PBST). A two-fold dilution series of exemplified antibodies, along with IgG4 and IgG1 isotype control antibodies, was generated starting at 20 nM in Casein-PBS. 100 µL of the each dilution series sample was added to a well for 30 min at 37° C. with gentle shaking. The plate was then washed three times with PBST. A 100 nM solution of biotinylated recombinant human NGF (btNGF) was prepared in Casein-PBS buffer, and 100 µL/well was added to the plate and incubated for 75 min at 37° C. with gentle shaking. The plate was then washed three times with PBST. A 1:3500 dilution of a 1 mg/mL stock solution of streptavidin-HRP (Thermo Scientific, #21130) in Casein-PBS was prepared and 100 was added to each well for 20 min at 37° C. with gentle shaking. The plate was washed three times with PBST. A 100 µL solution of 1:1 TMB:$H_2O_2$ (Thermo Scientific, #1854050, #1854060) was added to each well and incubated for 3 min. The reaction was stopped by addition of 100 µL of 1M $H_3PO_4$ to each well. The absorbance at 450 nm (Abs450) was measured using a SpectraMax 340PC plate reader (Molecular Devices). The Abs450 was plotted versus the antibody concentration, and a four parameter curve fit is determined using SigmaPlot 12.5 (Systat Software Inc.) to give the $IC_{50}$ values.

Exemplified mAbs A-E, but not the IgG4 and IgG1 isotype control antibodies, block the binding of human TrkA to NGF in a dose-dependent manner within the antibody concentration range tested (as shown in the Table 11).

TABLE 11

Blocking of binding of human Trk A to NGF

|  | mAb A | mAb B | mAb C | mAb D | mAb E | IgG4 Control | IgG1 Control |
|---|---|---|---|---|---|---|---|
| Absorbance 450 nm | | | | | | | |
| +20 nM mAb | 0.20 | 0.15 | 0.15 | 0.19 | 0.19 | 1.12 | 1.13 |
| +10 nM mAb | 0.20 | 0.14 | 0.15 | 0.17 | 0.19 | 1.11 | 0.97 |
| +5 nM mAb | 0.20 | 0.15 | 0.16 | 0.19 | 0.21 | 1.08 | 1.10 |
| +2.5 nM mAb | 0.21 | 0.16 | 0.15 | 0.16 | 0.19 | 1.07 | 1.17 |
| +1.25 nM mAb | 0.26 | 0.17 | 0.16 | 0.19 | 0.25 | 1.03 | 1.04 |
| +0.63 nM mAb | 0.38 | 0.25 | 0.30 | 0.38 | 0.41 | 1.13 | 1.14 |
| +0.31 pM mAb | 0.73 | 0.55 | 0.56 | 0.67 | 0.68 | 1.14 | 1.19 |
| +0.16 nM mAb | 0.87 | 0.70 | 0.77 | 0.89 | 0.92 | 1.13 | 1.12 |
| +0.08 nM mAb | 1.03 | 0.75 | 0.92 | 0.96 | 1.05 | 1.14 | 1.16 |

TABLE 11-continued

Blocking of binding of human Trk A to NGF

|  | mAb A | mAb B | mAb C | mAb D | mAb E | IgG4 Control | IgG1 Control |
|---|---|---|---|---|---|---|---|
| +0.04 nM mAb | 1.09 | 0.87 | 1.03 | 1.00 | 1.04 | 1.15 | 1.10 |
| +0.02 nM mAb | 1.11 | 0.97 | 0.97 | 1.05 | 1.10 | 1.13 | 1.14 |
| +0 nM mAb | 1.06 | 0.92 | 1.04 | 1.00 | 1.06 | 1.15 | 1.11 |
| IC50 from curve fits | | | | | | | |
| IC50 (nM) | 0.34 | 0.27 | 0.28 | 0.37 | 0.35 | | |

Example 9. Engineering, Expression, and Purification of mAb 1 and mAb 2

Expression vectors for the mammalian expression of mAb 1 were generated using the light chain sequence (Sequence ID #29) and heavy chain sequence (Sequence ID #57) provided in patent WO2016/087677 A1. Thus, mAb 1 has a light chain sequence defined by Sequence ID #29 and a heavy chain sequence defined by Sequence ID #57 of WO2016/087677 A1. Expression vectors for the mammalian expression of mAb 2 were generated using the light chain sequence (Sequence ID #91) and heavy chain sequence (Sequence ID #90) provided in patent US2013/0336964 A1. Thus, mAB2 has a light chain sequence defined by Sequence ID #91 and a heavy chain sequence defined by Sequence ID #90 of U.S. Patent Application Publication No. 2013/0336964.

These antibodies can be biosynthesized, purified, and formulated for administration by well-known methods. An appropriate host cell, such as Chinese hamster ovarian cells (CHO), is either transiently or stably transfected with an expression system for secreting antibodies using a predetermined HC:LC vector ratio if two vectors are used, or a single vector system encoding both heavy chain and light chain. Vectors suitable for expression and secretion of antibodies from these commonly-used host cells are well-known. Following expression and secretion of the antibody, the medium is clarified to remove cells. Clarified medium is applied to a Protein A affinity column that has been equilibrated with a compatible buffer, such as PBS (pH 7.4). The column is washed with buffer supplemented with 1M NaCl to remove nonspecific binding components. Bound antibody is eluted, for example, with sodium citrate at pH~3.5 and fractions are neutralized with 1M 2-amino-2-(hydroxymethyl)propane-1, 3-diol (Tris) buffer. Antibody fractions are detected, such as by sodium dodecyl sulfate polyacrylamide gel electrophoresis (SDS-PAGE) or analytical size-exclusion, and then are pooled. Soluble aggregate and multimers may be effectively removed by common techniques, including size exclusion, hydrophobic interaction, ion exchange, or hydroxyapatite chromatography. An exemplified antibody of the present invention is concentrated and/or sterile filtered using common techniques. The purity of exemplified antibody after these chromatography steps is greater than 95% and samples may be immediately frozen at −70° C. or stored at 4° C. for several months. The ability of mAb 1 and mAb 2 to bind to and/or inhibit signaling of TrkA can be assessed according to Examples 10-12.

Example 10. Binding Kinetics and Affinity for mAb B, mAb 1 and mAb 2

The binding kinetics and affinity of exemplified antibodies to human, cynomolgus monkey, rat, mouse, and rabbit TrkA are determined as described below using a surface plasmon resonance assay on a BIACORE™ 8K instrument (GE Healthcare). Two different isoforms of human TrkA (isoform 1 and isoform 2) are evaluated along with human TrkB and human TrkC. The BIACORE™ 8K is primed with HBS-EP+ running buffer [10 mM 2-[4-(2-hydroxyethyl) piperazin-1-yl]ethanesulfonic acid (Hepes pH 7.4, 150 mM NaCl, 3 mM ethylenediaminetetraacetic acid (EDTA), 0.05% polysorbate 20 surfactant (P20, TWEEN® 20)]. The analysis temperature is set at 37° C. and the sample compartment is set at 15° C. Binding kinetics and affinities are obtained using a parallel kinetics assay with an antibody capture method. Antibodies are captured onto a Series-S Sensor Protein A CM5 chip (GE Healthcare). For each channel, Flow Cell 1 (FC1) is designated as a buffer reference and Flow Cell 2 (FC2) is designated for antibody capture. All FC2 on all eight channels are set to capture approximately 89 response units (RU) of antibody at a flow rate of 10 µL/min. All antibody samples are prepared at 5 µg/mL by dilution into the running buffer. The human TrkA Isoform 2 analyte was prepared at a final concentration of 400, 200, 100, 50, 25, 12.5, 6.25, and 3.125 nM by dilution into the running buffer. Before the analysis cycle, the chip is regenerated with 3 injections of glycine (pH~1.5) at 100 µL/min for a contact time of 15 seconds on FC1 and FC2 in order to clean the surface of the chip. Regeneration is followed by a conditioning step consisting of (1) 5 µg/mL of an IgG4 isotype control antibody at 5 µL/min for 15 seconds on FC2; (2) running buffer at 30 µL/min for 250 seconds and dissociation for 600 seconds on FC1 and FC2; (3) chip surface regeneration with an injection of glycine (pH~1.5) at 100 µL/min for 15 seconds. Each analysis cycle consists of: (1) capturing the test antibody on all eight FC2, where all eight respective FC1 pairs are used as a buffer reference, at 10 µL/min; (2) running buffer wash step; (3) injection of TrkA analyte at 100 µL/min for 120 seconds on channels 1-8 in order of descending concentration; (4) return to buffer flow for a dissociation time of 600 seconds; (5) regeneration of the chip surface with two injections of glycine (pH~1.5), at 100 µL/min for 15 seconds per injection; (6) final running buffer wash step. This is repeated for each antibody evaluated. Data is processed using predefined antibody parallel kinetics with reference subtraction and fit to a 1:1 binding model using BIACORE™ 8K evaluation software (version 1.1.1.7442) to determine the association rate (on-rate, kon, $M^{-1}s^{-1}$ units) and the dissociation rate (off-rate, koff, $s^{-1}$ units). The equilibrium dissociation constant ($K_D$) is calculated from the relationship $K_D=k_{off}/k_{on}$, in molar units. The average (Avg) $K_D$ and error, reported as the standard deviation (SD), is determined from three independent experiments. Exemplified antibodies mAb B and mAb 1 demonstrate concentration-dependent binding to human TrkA. However, exemplified antibody mAb 2 shows no observable binding signal at the highest concentration of human TrkA injected (400 nM), and the binding response signal does not reach the theoretical half-maximal response signal. As a result, the $K_D$ of mAb 2 to human TrkA is estimated to be >400 nM. The results are shown in Table 12.

TABLE 12

BIACORE ™ binding kinetics and affinity of mAb B, mAb 1, and mAb 2

| Antibody | Analyte | $k_{on}$ (1/Ms) Avg ± SD | $k_{off}$ (1/s) Avg ± SD | $K_D$ (nM) Avg ± SD | # Replicates |
|---|---|---|---|---|---|
| mAb B | Human TrkA Isoform 2 | 1.6 ± 0.3 E5 | 1.2 ± 0.01 E-3 | 7.7 ± 1.4 | 3 |
| mAb 1 | Human TrkA Isoform 2 | 8.8 ± 1.5 E4 | 5.9 ± 0.8 E-3 | 70.0 ± 22.6 | 3 |
| mAb 2 | Human TrkA Isoform 2 | | | $K_D$ > 400 nM | 3 |

Example 11. Inhibition of NGF-Induced Phosphorylation of Human TrkA of mAb 1 and mAb B Inhibition of human NGF-stimulated phosphorylation of TrkA after a 1 or 24 hour pretreatment of antibody is assessed in cells that were transfected and express human TrkA receptor standard fibroblast cells (3T3) background. Methods are as described for example 4 with the following exceptions. Cells are seeded into a standard 24 well plate at 800,000 cells per well in standard growth media and placed in a 37° C./5% $CO_2$ incubator for 1.5 to 2 hours to allow cell adherence. Exemplified mAb B, an IgG4 control mAb, or proported TrkA receptor antibody mAb 1 were added to the media at a final concentration of 1 µM either 1 hour or 24 hours prior to addition of media or human β-NGF to give a final concentration 10 µg/mL. Media is removed after a 5 minute incubation at room temperature. One mL of Cell Lysis buffer described above is added, cells scraped and the homogenate transferred to a 1.5 mL Eppendorf tube and frozen on dry ice and stored at −80° C. Samples are thawed supernatants resulting from centrifugation at 4° C. for 15 minutes at 12,000 relative centrifugal force (RCF) are analyzed for protein concentration and equivalent protein amounts analyzed by ELISA methods to measure pTrkA, using methods described in Price et al (J Neurosci Methods 282:34-42, 2017), as detailed in example 4.

Resulting counts per second (CPS) are in the table 13 below:

TABLE 13

Stimulation or inhibition of NGF-induced phosphorylation of human TrkA.

|  | IgG4 control | mAb B | mAb 1 |
|---|---|---|---|
| Media only | 27600 | 26112 | 21320 |
| +mAb 1 hr | 28392 | 46576 | 30292 |
| +mAb 24 hr | 28700 | 45280 | 50588 |
| NGF | 292400 | 170212 | 147624 |
| NGF + mAb 1 hr | 238000 | 81504 | 117536 |
| NGF + mAb 24 hr | 289620 | 78156 | 177412 |

As seen from the results in Table X, the exemplified mAb B inhibited the NGF-induced phosphorylation of human TrkA to a similar extent when preincubated for either 1 or 24 hours. In contrast, mAb 1 failed to inhibit NGF-induced phosphorylation of human TrkA when preincubated with the cells for 1 or 24 hours.

Example 12. Blocking the Binding of Human Trk A to NGF for mAb B and mAb 1

Each row of a 96-well high-binding clear-bottom microtiter plate (Microlon, #655061) was coated overnight at 4° C. with 100 µL/well of recombinant human TrkA protein, diluted to 2 µg/mL in phosphate buffered saline, pH 7.2 (PBS). The next day, the coating solution was removed, and the plate was blocked with 150 µL of Casein-PBS (Thermo Scientific, #37528) for 1 hour at 25° C. with gentle shaking. The plate was then washed three times with PBS supplemented with 0.05% Tween20 (PBST). A three-fold dilution series of mAb B, mAb 1, and IgG4 isotype control mAb were generated starting at 300 nM in Casein-PBS. 100 µL of the each dilution series sample was added to a well for 30 min at 37° C. with gentle shaking. The plate was then washed three times with PBST. A 100 nM solution of biotinylated recombinant human NGF (btNGF) was prepared in Casein-PBS buffer, and 100 µL/well was added to the plate and incubated for 75 min at 37° C. with gentle shaking. A Casein-PBS buffer control row was included where btNGF was left out of the sample to assess background signal. The plate was then washed three times with PBST. A 1:3500 dilution of a 1 mg/mL stock solution of streptavidin-HRP (Thermo Scientific, #21130) in Casein-PBS was prepared and 100 µL was added to each well for 20 min at 37° C. with gentle shaking. The plate was washed three times with PBST. A 100 µL solution of 1:1 TMB:$H_2O_2$ (Thermo Scientific, #1854050, #1854060) was added to each well and incubated for 3 min. The reaction was stopped by addition of 100 µL of 1M $H_3PO_4$ to each well. The absorbance at 450 nm (Abs450) was measured using a SpectraMax 340PC plate reader (Molecular Devices). The Abs450 was plotted versus the antibody concentration. Complete blocking of TrkA binding to NGF was determined by whether or not the Abs450 reached the level of the buffer baseline at the highest antibody concentration tested. Results are summarized in Table 14.

Exemplified mAb B exhibited complete blocking of TrkA to NGF in a dose-dependent manner as the binding signal reached the buffer control baseline at the highest antibody concentration tested. The molecule mAb 1 did not exhibit complete blocking of TrkA to NGF within the concentration range tested as the binding signal did not reach the buffer control baseline at the highest antibody concentration tested. Instead, the binding signal of mAb 1 plateaued at binding signal that was higher than the buffer control baseline. This suggests that mAb 1 is a partial blocker of TrkA binding to NGF. The IgG4 isotype control mAb does not block the TrkA binding to NGF within the concentration range tested.

TABLE 14

Blocking of binding of human Trk A to NGF

| Antibody Concentration (nM) | Absorbance (450 nm) | | | |
|---|---|---|---|---|
| | mAb B | mAb 1 | IgG4 Control | Buffer Control |
| 300 | 0.08 | 0.20 | 0.40 | 0.10 |
| 100 | 0.08 | 0.19 | 0.39 | 0.10 |
| 33.3 | 0.08 | 0.19 | 0.41 | 0.12 |
| 11.1 | 0.09 | 0.22 | 0.40 | 0.11 |
| 3.7 | 0.16 | 0.27 | 0.43 | 0.12 |
| 1.24 | 0.28 | 0.34 | 0.43 | 0.12 |
| 0.41 | 0.33 | 0.36 | 0.42 | 0.18 |
| 0.14 | 0.36 | 0.38 | 0.42 | 0.13 |
| 0.05 | 0.37 | 0.39 | 0.40 | 0.13 |
| 0.015 | 0.36 | 0.38 | 0.41 | 0.12 |
| 0.005 | 0.36 | 0.41 | 0.40 | 0.12 |
| 0 | 0.36 | 0.38 | 0.41 | 0.11 |

Sequences

Exemplified HC #1 (Human IgG4PAA/Kappa) (SEQ ID NO: 1)
EVQLVESGGGLVKPGGSLRLSCAASGFTFSGVSINWVRQAPGKGLEWVSSETTSS
GTIYYADSVKGRFTISRDNAKNSLYLQMNSLRAEDTAVYYCARSYYYGMDVWG
QGTTVTVSSASTKGPSVFPLAPCSRSTSESTAALGCLVKDYFPEPVTVSWNSGALT
SGVHTFPAVLQSSGLYSLSSVVTVPSSSLGTKTYTCNVDHKPSNTKVDKRVESKY
GPPCPPCPAPEAAGGPSVFLFPPKPKDTLMISRTPEVTCVVVDVSQEDPEVQFNW
YVDGVEVHNAKTKPREEQFNSTYRVVSVLTVLHQDWLNGKEYKCKVSNKGLPS
SIEKTISKAKGQPREPQVYTLPPSQEEMTKNQVSLTCLVKGFYPSDIAVEWESNGQ
PENNYKTTPPVLDSDGSFFLYSRLTVDKSRWQEGNVFSCSVMHEALHNHYTQKS
LSLSLG Exemplified HC #2 (Human IgG1EN/Kappa) (SEQ ID NO: 2)
EVQLVESGGGLVKPGGSLRLSCAASGFTFSGVSINWVRQAPGKGLEWVSSETTSS
GTIYYADSVKGRFTISRDNAKNSLYLQMNSLRAEDTAVYYCARSYYYGMDVWG
QGTTVTVSSASTKGPSVFPLAPSSKSTSGGTAALGCLVKDYFPEPVTVSWNSGAL
TSGVHTFPAVLQSSGLYSLSSVVTVPSSSLGTQTYICNVNHKPSNTKVDKRVEPKS
CDKTHTCPPCPAPEAEGAPSVFLFPPKPKDTLMISRTPEVTCVVVDVSHEDPEVKF
NWYVDGVEVHNAKTKPREEQYNSTYRVVSVLTVLHQDWLNGKEYKCKVSNKA
LPSSIEKTISKAKGQPREPQVYTLPPSREEMTKNQVSLTCLVKGFYPSDIAVEWES
NGQPENNYKTTPPVLDSDGSFFLYSKLTVDKSRWQQGNVFSCSVMHEALHNHY
TQKSLSLSPGK Exemplified HCDR1 (SEQ ID NO: 3)
AASGFTFSGVSIN Exemplified HCDR2 (SEQ ID NO: 4)
SETTSSGTIYYADSVKG Exemplified HCDR3 (SEQ ID NO: 5)
ARSYYYGMDV Exemplified LC (SEQ ID NO: 6)
DIVMTQTPLSSPVTLGQPASISCRSSQSLVHRX$_{aa}$GNTYLSWLQQRPGQPPRLLIYKI
SNRFSGVPDRFSGSGAGTDFTLKISRVEAEDVGVYYCMQARQFPLTFGGGTKVEI
KRTVAAPSVFIFPPSDEQLKSGTASVVCLLNNFYPREAKVQWKVDNALQSGNSQ
ESVTEQDSKDSTYSLSSTLTLSKADYEKHKVYACEVTHQGLSSPVTKSFNRGEC
wherein X$_{aa}$ at residue 33 is one of N, A or Q Exemplified LCDR1 (SEQ ID NO: 7)
RSSQSLVHRX$_{aa}$GNTYLS
wherein X$_{aa}$ at residue 10 is one of N, A or Q Exemplified LCDR2 (SEQ ID NO: 8)
YKISNRFS Exemplified LCDR3 (SEQ ID NO: 9)
MQARQFPLT Exemplified HCVR (SEQ ID NO: 10)
EVQLVESGGGLVKPGGSLRLSCAASGFTFSGVSINWVRQAPGKGLEWVSSETTSS
GTIYYADSVKGRFTISRDNAKNSLYLQMNSLRAEDTAVYYCARSYYYGMDVWG
QGTTVTVSS Exemplified LCVR (SEQ ID NO: 11)
DIVMTQTPLSSPVTLGQPASISCRSSQSLVHRX$_{aa}$GNTYLSWLQQRPGQPPRLLIYKI
SNRFSGVPDRFSGSGAGTDFTLKISRVEAEDVGVYYCMQARQFPLTFGGGTKVEI
K
wherein X$_{aa}$ at residue 33 is one of N, A or Q Light Chain DNA Sequence For mAb A (Unoptimized DNA) (SEQ ID NO: 12)
(Unoptimized)
GATATTGTGATGACCCAGACTCCACTCTCCTCACCTGTCACCCTTGGACAGCC
GGCCTCCATCTCCTGCAGGTCTAGTCAAAGTCTCGTACACAGAGCTGGAAAC
ACCTACTTGAGTTGGCTTCAGCAGAGGCCAGGCCAGCCTCCAAGACTCCTAAT
TTATAAGATTTCTAACCGGTTCTCTGGGGTCCCAGACAGATTCAGTGGCAGTG
GGGCAGGGACAGATTTCACACTGAAAATCAGCAGGGTGGAAGCTGAGGATGT
CGGAGTTTATTATTGCATGCAAGCTAGACAATTTCCGCTCACTTTCGGCGGAG
GGACCAAGGTGGAGATCAAACGGACCGTGGCTGCACCATCTGTCTTCATCTTC
CCGCCATCTGATGAGCAGTTGAAATCTGGAACTGCCTCTGTTGTGTGCCTGCT
GAATAACTTCTATCCCAGAGAGGCCAAAGTACAGTGGAAGGTGGATAACGCC
CTCCAATCGGGTAACTCCCAGGAGAGTGTCACAGAGCAGGACAGCAAGGACA
GCACCTACAGCCTCAGCAGCACCCTGACGCTGAGCAAAGCAGACTACGAGAA
ACACAAAGTCTACGCCTGCGAAGTCACCCATCAGGGCCTGAGCTCGCCCGTC
ACAAAGAGCTTCAACAGGGGAGAGTGC Heavy Chain DNA Sequence For mAb A (Unoptimized DNA) (SED ID NO: 13)
(Unoptimized)
GAGGTGCAGCTGGTGGAGTCTGGAGGAGGCCTGGTCAAGCCTGGGGGGTCCC
TGAGACTCTCCTGTGCAGCCTCTGGATTCACCTTCAGTGGCGTCAGCATAAAC

| Sequences |
|---|
| TGGGTCCGCCAGGCTCCAGGGAAGGGGCTGGAGTGGGTCTCATCCGAGACTA
CAAGTAGTGGTACAATATACTACGCAGACTCAGTGAAGGGCCGATTCACCAT
CTCCAGAGACAACGCCAAGAACTCACTGTATCTGCAAATGAACAGCCTGAGA
GCCGAGGACACGGCTGTGTATTACTGTGCGAGAAGCTACTACTACGGTATGG
ACGTCTGGGGCCAAGGGACCACGGTCACCGTCTCCTCAGCCTCCACCAAGGG
CCCATCGGTCTTCCCGCTAGCGCCCTGCTCCAGGAGCACCTCCGAGAGCACAG
CCGCCCTGGGCTGCCTGGTCAAGGACTACTTCCCCGAACCGGTGACGGTGTCG
TGGAACTCAGGCGCCCTGACCAGCGGCGTGCACACCTTCCCGGCTGTCCTACA
GTCCTCAGGACTCTACTCCCTCAGCAGCGTGGTGACCGTGCCCTCCAGCAGCT
TGGGCACGAAGACCTACACCTGCAACGTAGATCACAAGCCCAGCAACACCAA
GGTGGACAAGAGAGTTGAGTCCAAATATGGTCCCCCATGCCCACCCTGCCCA
GCACCTGAGGCCGCCGGGGGACCATCAGTCTTCCTGTTCCCCCCAAAACCCA
AGGACACTCTCATGATCTCCCGGACCCCTGAGGTCACGTGCGTGGTGGTGGA
CGTGAGCCAGGAAGACCCCGAGGTCCAGTTCAACTGGTACGTGGATGGCGTG
GAGGTGCATAATGCCAAGACAAAGCCGCGGGAGGAGCAGTTCAACAGCACG
TACCGTGTGGTCAGCGTCCTCACCGTCCTGCACCAGGACTGGCTGAACGGCA
AGGAGTACAAGTGCAAGGTCTCCAACAAAGGCCTCCCGTCCTCCATCGAGAA
AACCATCTCCAAAGCCAAAGGGCAGCCCCGAGAGCCACAGGTGTACACCCTG
CCCCCATCCCAGGAGGAGATGACCAAGAACCAGGTCAGCCTGACCTGCCTGG
TCAAAGGCTTCTACCCCAGCGACATCGCCGTGGAGTGGGAAAGCAATGGGCA
GCCGGAGAACAACTACAAGACCACGCCTCCCGTGCTGGACTCCGACGGCTCC
TTCTTCCTCTACAGCAGGCTAACCGTGGACAAGAGCAGGTGGCAGGAGGGGA
ATGTCTTCTCATGCTCCGTGATGCATGAGGCTCTGCACAACCACTACACACAG
AAGAGCCTCTCCCTGTCTCTGGGT |

Light Chain DNA Sequence For mAb B (Codon Optimized) (SED ID NO: 14)
(Optimized)
GACATCGTGATGACCCAGACCCCTTTATCCTCCCCCGTTACACTGGGCCAGCC
CGCTTCCATCTCTTGTCGTTCCTCCCAGTCTTTAGTGCATCGTGCTGGCAACAC
CTATTTATCTTGGCTGCAGCAGAGGCCCGGTCAGCCTCCTCGTCTGCTGATCT
ACAAGATCAGCAACCGGTTCTCCGGCGTGCCCGATCGTTTTTCCGGCTCCGGA
GCCGGCACCGATTTCACTTTAAAGATCTCTCGTGTGGAGGCCGAGGATGTGG
GCGTGTACTACTGCATGCAAGCTCGTCAGTTCCCTCTGACCTTCGGCGGCGGC
ACCAAGGTGGAGATCAAGCGTACGGTGGCTGCACCATCTGTCTTCATCTTCCC
GCCATCTGATGAGCAGTTGAAATCTGGAACTGCCTCTGTTGTGTGCCTGCTGA
ATAACTTCTATCCCAGAGAGGCCAAAGTACAGTGGAAGGTGGATAACGCCCT
CCAATCGGGTAACTCCCAGGAGAGTGTCACAGAGCAGGACAGCAAGGACAG
CACCTACAGCCTCAGCAGCACCCTGACGCTGAGCAAAGCAGACTACGAGAAA
CACAAAGTCTACGCCTGCGAAGTCACCCATCAGGGCCTGAGCTCGCCCGTCA
CAAAGAGCTTCAACAGGGGAGAGTGT Heavy Chain DNA Sequence For mAb B and mAb C (Codon Optimized) (SEQ
ID NO: 15) (Optimized)
GAGGTGCAGCTCGTGGAGTCCGGCGGAGGACTGGTGAAGCCCGGTGGCTCTT
TAAGGCTGTCTTGTGCCGCTTCCGGCTTCACCTTCTCCGGCGTGTCCATCAACT
GGGTGAGGCAAGCTCCCGGTAAGGGTTTAGAGTGGGTGTCCTCCGAGACCAC
CTCCTCCGGCACCATCTACTACGCCGACTCCGTGAAGGGCCGGTTCACCATCT
CTCGTGACAACGCCAAGAACTCTTTATATTTACAGATGAACTCTTTAAGGGCC
GAGGACACCGCCGTGTACTACTGCGCGTCGTTCCTACTACTACGGCATGGACGT
GTGGGGCCAAGGTACCACCGTGACAGTCTCCTCCGCTAGCACCAAGGGCCCA
TCCGTCTTCCCCCTGGCGCCCTGCTCCAGGAGCACCTCCGAGAGCACAGCCGC
CCTGGGCTGCCTGGTCAAGGACTACTTCCCCGAACCGGTGACGGTGTCGTGG
AACTCAGGCGCCCTGACCAGCGGCGTGCACACCTTCCCGGCTGTCCTACAGTC
CTCAGGACTCTACTCCCTCAGCAGCGTGGTGACCGTGCCCTCCAGCAGCTTGG
GCACGAAGACCTACACCTGCAACGTAGATCACAAGCCCAGCAACACCAAGGT
GGACAAGAGAGTTGAGTCCAAATATGGTCCCCCATGCCCACCATGCCCAGCA
CCTGAGGCAGCTGGGGGACCATCAGTCTTCCTGTTCCCCCCAAAACCCAAGG
ACACTCTCATGATCTCCCGGACCCCTGAGGTCACGTGCGTGGTGGTGGACGTG
AGCCAGGAAGACCCCGAGGTCCAGTTCAACTGGTACGTGGATGGCGTGGAGG
TGCATAATGCCAAGACAAAGCCGCGGGAGGAGCAGTTCAACAGCACGTACCG
TGTGGTCAGCGTCCTCACCGTCCTGCACCAGGACTGGCTGAACGGCAAGGAG
TACAAGTGCAAGGTCTCCAACAAAGGCCTCCCGTCCTCCATCGAGAAAACCA
TCTCCAAAGCCAAAGGGCAGCCCCGAGAGCCACAGGTGTACACCCTGCCCCC
ATCCCAGGAGGAGATGACCAAGAACCAGGTCAGCCTGACCTGCCTGGTCAAA
GGCTTCTACCCCAGCGACATCGCCGTGGAGTGGGAGAGCAATGGGCAGCCGG
AGAACAACTACAAGACCACGCCTCCCGTGCTGGACTCCGACGGCTCCTTCTTC
CTCTACAGCAGGCTAACCGTGGACAAGAGCAGGTGGCAGGAGGGGAATGTCT
TCTCATGCTCCGTGATGCATGAGGCTCTGCACAACCACTACACACAGAAGAG
CCTCTCCCTGTCTCTGGGT Light Chain DNA Sequence For mAb C (Codon Optimized) (SEQ ID NO: 16)
(Optimized)
GACATCGTGATGACCCAGACCCCTTTATCCTCCCCCGTTACACTGGGCCAGCC
CGCTTCCATCAGCTGTAGGTCCTCCCAGTCTTTAGTGCATCGTCAAGGTAACA
CATATTTATCTTGGCTGCAGCAGAGGCCCGGTCAACCTCCTCGGCTGCTGATC
TACAAGATCTCCAACCGGTTCTCCGGCGTGCCCGATAGGTTCTCCGGCTCCGG
CGCTGGCACCGATTTCACTTTAAAGATCTCTCGTGTGGAGGCTGAGGATGTGG

```
GCGTGTACTACTGCATGCAAGCTCGTCAGTTCCCTTTAACCTTCGGAGGCGGC
ACCAAGGTGGAGATCAAGCGTACGGTGGCTGCACCATCTGTCTTCATCTTCCC
GCCATCTGATGAGCAGTTGAAATCTGGAACTGCCTCTGTTGTGTGCCTGCTGA
ATAACTTCTATCCCAGAGAGGCCAAAGTACAGTGGAAGGTGGATAACGCCCT
CCAATCGGGTAACTCCCAGGAGAGTGTCACAGAGCAGGACAGCAAGGACAG
CACCTACAGCCTCAGCAGCACCCTGACGCTGAGCAAAGCAGACTACGAGAAA
CACAAAGTCTACGCCTGCGAAGTCACCCATCAGGGCCTGAGCTCGCCCGTCA
CAAAGAGCTTCAACAGGGGAGAGTGT
```

Light Chain DNA Sequence For mAb D (Codon Optimized) (SEQ ID NO: 17) (Optimized)
```
GACATCGTGATGACCCAGACCCCTTTATCCTCCCCCGTTACACTGGGCCAGCC
CGCTTCCATCTCTTGTCGTTCCTCCCAGTCTTTAGTGCATCGTGCTGGCAACAC
CTATTTATCTTGGCTGCAGCAGAGGCCCGGTCAGCCTCCTCGTCTGCTGATCT
ACAAGATCAGCAACCGGTTCTCCGGCGTGCCCGATCGTTTTTCCGGCTCCGGA
GCCGGCACCGATTTCACTTTAAAGATCTCTCGTGTGGAGGCCGAGGATGTGG
GCGTGTACTACTGCATGCAAGCTCGTCAGTTCCCTCTGACCTTCGGCGGCGGC
ACCAAGGTGGAGATCAAGCGTACGGTGGCTGCACCATCTGTCTTCATCTTCCC
GCCATCTGATGAGCAGTTGAAATCTGGAACTGCCTCTGTTGTGTGCCTGCTGA
ATAACTTCTATCCCAGAGAGGCCAAAGTACAGTGGAAGGTGGATAACGCCCT
CCAATCGGGTAACTCCCAGGAGAGTGTCACAGAGCAGGACAGCAAGGACAG
CACCTACAGCCTCAGCAGCACCCTGACGCTGAGCAAAGCAGACTACGAGAAA
CACAAAGTCTACGCCTGCGAAGTCACCCATCAGGGCCTGAGCTCGCCCGTCA
CAAAGAGCTTCAACAGGGGAGAGTGT
```

Light Chain DNA Sequence For mAb E (Codon Optimized) (SEQ ID NO: 18) (Optimized)
```
GACATCGTGATGACCCAGACCCCTTTATCCTCCCCCGTTACACTGGGCCAGCC
CGCTTCCATCAGCTGTAGGTCCTCCCAGTCTTTAGTGCATCGTCAAGGTAACA
CATATTTATCTTGGCTGCAGCAGAGGCCCGGTCAACCTCCTCGGCTGCTGATC
TACAAGATCTCCAACCGGTTCTCCGGCGTGCCCGATAGGTTCTCCGGCTCCGG
CGCTGGCACCGATTTCACTTTAAAGATCTCTCGTGTGGAGGCTGAGGATGTGG
GCGTGTACTACTGCATGCAAGCTCGTCAGTTCCCTTTAACCTTCGGAGGCGGC
ACCAAGGTGGAGATCAAGCGTACGGTGGCTGCACCATCTGTCTTCATCTTCCC
GCCATCTGATGAGCAGTTGAAATCTGGAACTGCCTCTGTTGTGTGCCTGCTGA
ATAACTTCTATCCCAGAGAGGCCAAAGTACAGTGGAAGGTGGATAACGCCCT
CCAATCGGGTAACTCCCAGGAGAGTGTCACAGAGCAGGACAGCAAGGACAG
CACCTACAGCCTCAGCAGCACCCTGACGCTGAGCAAAGCAGACTACGAGAAA
CACAAAGTCTACGCCTGCGAAGTCACCCATCAGGGCCTGAGCTCGCCCGTCA
CAAAGAGCTTCAACAGGGGAGAGTGT
```

Heavy Chain DNA Sequence For mAb D and mAb E (Codon Optimized) (SEQ ID NO: 19) (Optimized)
```
GAGGTGCAGCTCGTGGAGTCCGGCGGAGGACTGGTGAAGCCCGGTGGCTCTT
TAAGGCTGTCTTGTGCCGCTTCCGGCTTCACCTTCTCCGGCGTGTCCATCAACT
GGGTGAGGCAAGCTCCCGGTAAGGGTTTAGAGTGGGTGTCCTCCGAGACCAC
CTCCTCCGGCACCATCTACTACGCCGACTCCGTGAAGGGCCGGTTCACCATCT
CTCGTGACAACGCCAAGAACTCTTTATATTTACAGATGAACTCTTTAAGGGCC
GAGGACACCGCCGTGTACTACTGCGCTCGTTCCTACTACTACGGCATGGACGT
GTGGGGCCAAGGTACCACCGTGACAGTCTCCTCCGCTAGCACCAAGGGCCCA
TCGGTCTTCCCCCTGGCACCCTCCTCCAAGAGCACCTCTGGGGGCACAGCGGC
CCTGGGCTGCCTGGTCAAGGACTACTTCCCCGAACCGGTGACGGTGTCGTGG
AACTCAGGCGCCCTGACCAGCGGCGTGCACACCTTCCCGGCCGTCCTACAGTC
CTCAGGACTCTACTCCCTCAGCAGCGTGGTGACCGTGCCCTCCAGCAGCTTGG
GCACCCAGACCTACATCTGCAACGTGAATCACAAGCCCAGCAACACCAAGGT
GGACAAGCGGGTTGAGCCCAAATCTTGTGACAAAACTCACACATGCCCACCG
TGCCCAGCACCTGAAGCCGAGGGGGCACCGTCAGTCTTCCTCTTCCCCCCAAA
ACCCAAGGACACCCTCATGATCTCCCGGACCCCTGAGGTCACATGCGTGGTG
GTGGACGTGAGCCACGAAGACCCTGAGGTCAAGTTCAACTGGTACGTGGACG
GCGTGGAGGTGCATAATGCCAAGACAAAGCCGCGGGAGGAGCAGTACAACA
GCACGTACCGTGTGGTCAGCGTCCTCACCGTCCTGCACCAGGACTGGCTGAAT
GGCAAGGAGTACAAGTGCAAGGTCTCCAACAAAGCCCTCCCATCCTCCATCG
AGAAAACCATCTCCAAAGCCAAAGGGCAGCCCCGAGAACCACAGGTGTACA
CCCTGCCCCCATCCCGGGAGGAGATGACCAAGAACCAGGTCAGCCTGACCTG
CCTGGTCAAAGGCTTCTATCCCAGCGACATCGCCGTGGAGTGGGAGAGCAAT
GGGCAGCCGGAGAACAACTACAAGACCACGCCTCCCGTGCTGGACTCCGACG
GCTCCTTCTTCCTCTACAGCAAGCTCACCGTGGACAAGAGCAGGTGGCAGCA
GGGGAACGTCTTCTCATGCTCCGTGATGCATGAGGCTCTGCACAACCACTACA
CGCAGAAGAGCCTCTCCCTGTCTCCGGGTAAA
```

Human TrkA Extracellular Domain Isoform 1 (33-414) (Purification Tag: N-terminal 8X Histidine) (SEQ ID NO: 20)
```
HHHHHHHHAAPCPDACCPHGSSGLRCTRDGALDSLHHLPGAENLTELYIENQQH
LQHLELRDLRGLGELRNLTIVKSGLRFVAPDAFHFTPRLSRLNLSFNALESLSWKT
VQGLSLQELVLSGNPLHCSCALRWLQRWEEEGLGGVPEQKLQCHGQGPLAHMP
NASCGVPTLKVQVPNASVDVGDDVLLRCQVEGRGLEQAGWILTELEQSATVMK
SGGLPSLGLTLANVTSDLNRKNVTCWAENDVGRAEVSVQVNVSFPASVQLHTA
```

| Sequences |
|---|
| VEMEIEWCIPFSVDGQPAPSLRWLFNGSVLNETSFIFTEFLEPAANETVRHGCLRL<br>NQPTHVNNGNYTLLAANPFGQASASIMAAFMDNPFEFNPEDPIPVSFSPVDTNSTS<br>GDPVEKKDET<br><br>Human TrkA Extracellular Domain Isoform 2 (33-408) (Purification<br>Tag: N-terminal 8X Histidine) (SEQ ID NO: 21)<br>HHHHHHHHAAPCPDACCPHGSSGLRCTRDGALDSLHHLPGAENLTELYIENQQH<br>LQHLELRDLRGLGELRNLTIVKSGLRFVAPDAFHFTPRLSRLNLSFNALESLSWKT<br>VQGLSLQELVLSGNPLHCSCALRWLQRWEEEGLGGVPEQKLQCHGQGPLAHMP<br>NASCGVPTLKVQVPNASVDVGDDVLLRCQVEGRGLEQAGWILTELEQSATVMK<br>SGGLPSLGLTLANVTSDLNRKNVTCWAENDVGRAEVSVQVNVSFPASVQLHTA<br>VEMEIRWCIPFSVDGQPAPSLRWLFNGSVLNETSFIFTEFLEPAANETVRHGCLRL<br>NQPTHVNNGNYTLLAANPFGQASASIIVIAAFMDNPFEFNPEDPIPDTNSTSGDPVE<br>KKDET<br><br>Human TrkB Extracellular Domain (32-430) (Purification Tag: N-<br>terminal 8X Histidine) (SEQ ID NO: 22)<br>HHHHHHHHCPTSCKCSASRIWCSDPSPGIVAFPRLEPNSVDPENITEIFIANQKRLE<br>IINEDDVEAYVGLRNLTIVDSGLKFVAHKAFLKNSNLQHINFTRNKLTSLSRKHFR<br>HLDLSELILVGNPFTCSCDIMWIKTLQEAKSSPDTQDLYCLNESSKNIPLANLQIPN<br>CGLPSANLAAPNLTVEEGKSITLSCSVAGDPVPNMYWDVGNLVSKHMNETSHTQ<br>GSLRITNISSDDSGKQISCVAENLVGEDQDSVNLTVHFAPTITFLESPTSDHEIWCIP<br>FTVKGNPKPALQWFYNGAILNESKYICTKIHVTNHTEYHGCLQLDNPTHMNNGD<br>YTLIAKNEYGKDEKQISAHFMGWPGIDDGANPNYPDVIYEDYGTAANDIGDTTN<br>RSNEIPSTDVTDKTGREH<br><br>Human TrkC Extracellular Domain (32-428) (Purification Tag: N-<br>terminal 8X Histidine) (SEQ ID NO: 23)<br>HHHHHHHHCPANCVCSKTEINCRRPDDGNLFPLLEGQDSGNSNGNASINITDISR<br>NITSIHIENWRSLHTLNAVDMELYTGLQKLTIKNSGLRSIQPRAFAKNPHLRYINLS<br>SNRLTTLSWQLFQTLSLRELQLEQNFFNCSCDIRWMQLWQEQGEAKLNSQNLYC<br>INADGSQLPLFRMNISQCDLPEISVSHVNLTVREGDNAVITCNGSGSPLPDVDWIV<br>TGLQSINTHQTNLNWTNVHAINLTLVNVTSEDNGFTLTCIAENVVGMSNASVAL<br>TVYYPPRVVSLEEPELRLEHCIEFVVRGNPPPTLHWLHNGQPLRESKIIHVEYYQE<br>GEISEGCLLFNKPTHYNNGNYTLIAKNPLGTANQTINGHFLKEPFPESTDNFILFDE<br>VSPTPPITVTHKPEED<br><br>Cynomolgus monkey TrkA Extracellular Domain (59-434) (Purification<br>Tag: N-terminal 8X Histidine) (SEQ ID NO: 24)<br>HHHHHHHHASPCPDACCPHGSSGLRCTRDGALDSLHHLPGAENLTELYIENQQH<br>LQHLELRDLRGLGELRNLTIVKSGLRFVAPDAFHFTPRLSRLNLSFNALESLSWKT<br>VQGLSLQELVLSGNPLHCSCALRWLQRWEEEGLGGVHEQKLQCHGQGPLAHMP<br>NASCGVPMLKVQVPNASVDVGDDVLLWCQVEGRGLEQAGWILTELEQSATVM<br>KSGALPSLGLTLANVTSDLNRKNVTCWAENDVGRAELSVQVNVSFPASVQLHTA<br>VEMBHWCIPFSVDGQPAPSLRWLFNGSVLNETSFIFTEFLEPAANETVRHGCLRL<br>NQPTHVNNGNYTLLAANPFGQASASIMAAFMDNPFEFNPEDPIPDTNSTSGDPVE<br>KKDET<br><br>Mouse TrkA Extracellular Domain (33-417 with 396-401 deletion)<br>(Purification Tag: N-terminal 8X Histidine) (SEQ ID NO: 25)<br>HHHHHHHHAASCREVCCPVGPSGLRCTRAGSLDTLRGLRGAGNLTELYVENQQ<br>HLQRLEFEDLQGLGELRSLTIVKSGLRFVAPDAFRFTPRLSHLNLSSNALESLSWK<br>TVQGLSLQDLTLSGNPLHCSCALFWLQRWEQEGLCGVHTQTLHDSGPGDQFLPL<br>GHNTSCGVPTVKIQMPNDSVEVGDDVFLQCQVEGLALQQADWILTELEGAATV<br>KKFGDLPSLGLILVNVTSDLNKKNVTCWAENDVGRAEVSVQVSVSFPASVHLGL<br>AVEQHHWCIPFSVDGQPAPSLRWLFNGSVLNETSFIFTQFLESALTNETMRHGCL<br>RLNQPTHVNNGNYTLLAANPYGQAASVMAAFMDNPFEFNPEDPIPDGNSTSRD<br>PVEKKDET<br><br>Rat TrkA Extracellular Domain (33-411) (Purification Tag: N-terminal<br>8X Histidine) (SEQ ID NO: 26)<br>HHHHHHHHAASCRETCCPVGPSGLRCTRAGTLNTLRGLRGAGNLTELYVENQR<br>DLQRLEFEDLQGLGELRSLTIVKSGLRFVAPDAFHFTPRLSHLNLSSNALESLSWK<br>TVQGLSLQDLTLSGNPLHCSCALLWLQRWEQEDLCGVYTQKLQGSGSGDQFLPL<br>GHNNSCGVPSVKIQMPNDSVEVGDDVFLQCQVEGQALQQADWILTELEGTATM<br>KKSGDLPSLGLTLVNVTSDLNKKNVTCWAENDVGRAEVSVQVSVSFPASVHLG<br>KAVEQHHWCIPFSVDGQPAPSLRWFFNGSVLNETSFIFTQFLESALTNETMRHGC<br>LRLNQPTHVNNGNYTLLAANPYGQAAASIMAAFMDNPFEFNPEDPIPDTNSTSRD<br>PVEKKDET<br><br>Rabbit TrkA Extracellular Domain (33-414) (Purification Tag: C-<br>terminal polyhistidine tag (unknown length)) (SED ID NO: 27)<br>AALCPDVCCPRGPSGLLCTRPGALDRLRHLPGIENLTELYLENQNLQHLTLGDLR<br>GLRELRNLAIVNSGLQSVATDAFRFTPRLSHLNLSFNALESLSWKTVQGLPLQEL<br>VLSGNSLRCSCALRWLQRWEEEGLAGVREQKLRCSESEPLALMPNASCGMPTLK<br>VQMPNGSVDVGDSVFLQCQVEGQGLEKAGWSLTELEELATVMIQKSEDLPTLRL<br>TLANVTSDLNRKNVTCWAENDVGRTEVSVQVNVSFPASVQLHTAVEMEIHWCIP |

-continued

| Sequences |
|---|
| FSVDGQPAPSLHWLFNGSVLNETSFIFTEFLEPAANETMRHGCLRLNQPTHVNNG<br>NYTLLATNPSGQAAASIMAAFMDNPFEFNPEDPIPVSFSPVDANSTSGDPVEKKD<br>E |

We claim:

1. An antibody that binds tropomysin receptor kinase (TrkA) comprising a heavy chain variable region (HCVR) and a light chain variable region (LCVR), wherein the HCVR comprises complementarity determining regions (CDRs) HCDR1, HCDR2, and HCDR3 and the LCVR comprises CDRs LCDR1, LCDR2, and LCDR3, wherein the amino acid sequence of HCDR1 is SEQ ID NO: 3, the amino acid sequence of HCDR2 is SEQ ID NO: 4, the amino acid sequence of HCDR3 is SEQ ID NO: 5, the amino acid sequence of LCDR1 is SEQ ID NO: 7, the amino acid sequence of LCDR2 is SEQ ID NO: 8, and the amino acid sequence of LCDR3 is SEQ ID NO: 9.

2. The antibody of claim 1, wherein $X_{aa}$ at residue 10 of SEQ ID NO: 7 is A.

3. The antibody of claim 1, wherein $X_{aa}$ at residue 10 of SEQ ID NO: 7 is Q.

4. The antibody of claim 1, wherein the amino acid sequence of the HCVR is SEQ ID NO: 10 and the amino acid sequence of the LCVR is SEQ ID NO: 11.

5. The antibody of claim 4, wherein $X_{aa}$ at residue 33 of SEQ ID NO: 11 is A.

6. The antibody of claim 4, wherein $X_{aa}$ at residue 33 of SEQ ID NO: 11 is Q.

7. A pharmaceutical composition comprising an antibody of claim 1 and one or more pharmaceutically acceptable carriers, diluents or excipients.

8. A method of treating pain comprising administering to a patient in need thereof the pharmaceutical composition of claim 7.

9. The method of claim 8, wherein the pain is one of post-surgical pain, neuropathic pain, rheumatoid arthritis pain and osteoarthritis pain.

10. The method of claim 8, wherein the pain is chronic pain.

11. A method of treating pain comprising administering to a patient in need thereof an effective amount of an antibody of claim 1.

12. The method of claim 11, wherein the pain is one of post-surgical pain, neuropathic pain, rheumatoid arthritis pain and osteoarthritis pain.

13. The method of claim 11, wherein the pain is chronic pain.

14. An antibody that binds tropomysin receptor kinase (TrkA) comprising a heavy chain (HC) and a light chain (LC), wherein the amino acid sequence of the HC is selected from the group consisting of SEQ ID NO: 1 and SEQ ID NO: 2, and wherein and the amino acid sequence of the LC is SEQ ID NO: 6.

15. The antibody of claim 14, wherein there are two HCs, each of which have the amino acid sequence of SEQ ID NO: 1, and wherein there are two LCs, each of which has the amino acid sequence of SEQ ID NO: 6.

16. The antibody of claim 15, wherein $X_{aa}$ at residue 33 of SEQ ID NO: 6 is A.

17. The antibody of claim 15, wherein $X_{aa}$ at residue 33 of SEQ ID NO: 6 is Q.

18. The antibody of claim 14, wherein there are two HCs, each of which have the amino acid sequence of SEQ ID NO: 2, and wherein there are two LCs, each of which has the amino acid sequence of SEQ ID NO: 6.

19. The antibody of claim 18, wherein $X_{aa}$ at residue 33 of SEQ ID NO: 6 is A.

20. The antibody of claim 18, wherein $X_{aa}$ at residue 33 of SEQ ID NO: 6 is Q.

* * * * *

UNITED STATES PATENT AND TRADEMARK OFFICE
CERTIFICATE OF CORRECTION

PATENT NO. : 10,618,974 B2  
APPLICATION NO. : 16/281227  
DATED : April 14, 2020  
INVENTOR(S) : Catherine Brautigam Beidler, Daniel Scott Girard and Chetankumar Natvarial Patel Page 1 of 1

It is certified that error appears in the above-identified patent and that said Letters Patent is hereby corrected as shown below:

On the Title Page

In Column 2 item (57) (Abstract), Line 1, delete "tropomysin" and insert -- tropomyosin --

In the Claims

In Column 71, Line 2, in Claim 1, delete "tropomysin" and insert -- tropomyosin --

In Column 72, Line 11, in Claim 14, delete "tropomysin" and insert -- tropomyosin --

Signed and Sealed this  
Sixteenth Day of June, 2020

Andrei Iancu  
*Director of the United States Patent and Trademark Office*

SEQUENCE LISTING

<160> NUMBER OF SEQ ID NOS: 27

<210> SEQ ID NO 1
<211> LENGTH: 443
<212> TYPE: PRT
<213> ORGANISM: Artificial Sequence
<220> FEATURE:
<223> OTHER INFORMATION: Synthetic Construct

<400> SEQUENCE: 1

```
Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Gly Val
            20                  25                  30

Ser Ile Asn Trp Val Arg Gln Ala Pro Gly Lys Gly Leu Glu Trp Val
        35                  40                  45

Ser Ser Glu Thr Thr Ser Ser Gly Thr Ile Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Ser Tyr Tyr Tyr Gly Met Asp Val Trp Gly Gln Gly Thr Thr
            100                 105                 110

Val Thr Val Ser Ser Ala Ser Thr Lys Gly Pro Ser Val Phe Pro Leu
        115                 120                 125

Ala Pro Cys Ser Arg Ser Thr Ser Glu Ser Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Lys Thr Tyr Thr Cys Asn Val Asp His Lys Pro Ser Asn
        195                 200                 205

Thr Lys Val Asp Lys Arg Val Glu Ser Lys Tyr Gly Pro Pro Cys Pro
    210                 215                 220

Pro Cys Pro Ala Pro Glu Ala Ala Gly Gly Pro Ser Val Phe Leu Phe
225                 230                 235                 240

Pro Pro Lys Pro Lys Asp Thr Leu Met Ile Ser Arg Thr Pro Glu Val
                245                 250                 255

Thr Cys Val Val Val Asp Val Ser Gln Glu Asp Pro Glu Val Gln Phe
            260                 265                 270

Asn Trp Tyr Val Asp Gly Val Glu Val His Asn Ala Lys Thr Lys Pro
        275                 280                 285

Arg Glu Glu Gln Phe Asn Ser Thr Tyr Arg Val Val Ser Val Leu Thr
    290                 295                 300
```

```
Val Leu His Gln Asp Trp Leu Asn Gly Lys Glu Tyr Lys Cys Lys Val
305                 310                 315                 320

Ser Asn Lys Gly Leu Pro Ser Ser Ile Glu Lys Thr Ile Ser Lys Ala
            325                 330                 335

Lys Gly Gln Pro Arg Glu Pro Gln Val Tyr Thr Leu Pro Pro Ser Gln
            340                 345                 350

Glu Glu Met Thr Lys Asn Gln Val Ser Leu Thr Cys Leu Val Lys Gly
            355                 360                 365

Phe Tyr Pro Ser Asp Ile Ala Val Glu Trp Glu Ser Asn Gly Gln Pro
            370                 375                 380

Glu Asn Asn Tyr Lys Thr Thr Pro Pro Val Leu Asp Ser Asp Gly Ser
385                 390                 395                 400

Phe Phe Leu Tyr Ser Arg Leu Thr Val Asp Lys Ser Arg Trp Gln Glu
                405                 410                 415

Gly Asn Val Phe Ser Cys Ser Val Met His Glu Ala Leu His Asn His
            420                 425                 430

Tyr Thr Gln Lys Ser Leu Ser Leu Ser Leu Gly
            435                 440

<210> SEQ ID NO 2
<211> LENGTH: 447
<212> TYPE: PRT
<213> ORGANISM: Artificial Sequence
<220> FEATURE:
<223> OTHER INFORMATION: Synthetic Construct

<400> SEQUENCE: 2

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Gly Val
            20                  25                  30

Ser Ile Asn Trp Val Arg Gln Ala Pro Gly Lys Gly Leu Glu Trp Val
        35                  40                  45

Ser Ser Glu Thr Thr Ser Ser Gly Thr Ile Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Ser Tyr Tyr Tyr Gly Met Asp Val Trp Gly Gln Gly Thr Thr
            100                 105                 110

Val Thr Val Ser Ser Ala Ser Thr Lys Gly Pro Ser Val Phe Pro Leu
        115                 120                 125

Ala Pro Ser Ser Lys Ser Thr Ser Gly Gly Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
        195                 200                 205

Thr Lys Val Asp Lys Arg Val Glu Pro Lys Ser Cys Asp Lys Thr His
    210                 215                 220
```

```
Thr Cys Pro Pro Cys Pro Ala Pro Glu Ala Glu Gly Ala Pro Ser Val
225                 230                 235                 240

Phe Leu Phe Pro Pro Lys Pro Lys Asp Thr Leu Met Ile Ser Arg Thr
            245                 250                 255

Pro Glu Val Thr Cys Val Val Val Asp Val Ser His Glu Asp Pro Glu
        260                 265                 270

Val Lys Phe Asn Trp Tyr Val Asp Gly Val Glu Val His Asn Ala Lys
    275                 280                 285

Thr Lys Pro Arg Glu Glu Gln Tyr Asn Ser Thr Tyr Arg Val Val Ser
290                 295                 300

Val Leu Thr Val Leu His Gln Asp Trp Leu Asn Gly Lys Glu Tyr Lys
305                 310                 315                 320

Cys Lys Val Ser Asn Lys Ala Leu Pro Ser Ser Ile Glu Lys Thr Ile
            325                 330                 335

Ser Lys Ala Lys Gly Gln Pro Arg Glu Pro Gln Val Tyr Thr Leu Pro
        340                 345                 350

Pro Ser Arg Glu Glu Met Thr Lys Asn Gln Val Ser Leu Thr Cys Leu
    355                 360                 365

Val Lys Gly Phe Tyr Pro Ser Asp Ile Ala Val Glu Trp Glu Ser Asn
370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Lys Leu Thr Val Asp Lys Ser Arg
            405                 410                 415

Trp Gln Gln Gly Asn Val Phe Ser Cys Ser Val Met His Glu Ala Leu
        420                 425                 430

His Asn His Tyr Thr Gln Lys Ser Leu Ser Leu Ser Pro Gly Lys
    435                 440                 445

<210> SEQ ID NO 3
<211> LENGTH: 13
<212> TYPE: PRT
<213> ORGANISM: Artificial Sequence
<220> FEATURE:
<223> OTHER INFORMATION: Synthetic Construct

<400> SEQUENCE: 3

Ala Ala Ser Gly Phe Thr Phe Ser Gly Val Ser Ile Asn
1               5                   10

<210> SEQ ID NO 4
<211> LENGTH: 17
<212> TYPE: PRT
<213> ORGANISM: Artificial Sequence
<220> FEATURE:
<223> OTHER INFORMATION: Synthetic Construct

<400> SEQUENCE: 4

Ser Glu Thr Thr Ser Ser Gly Thr Ile Tyr Tyr Ala Asp Ser Val Lys
1               5                   10                  15

Gly

<210> SEQ ID NO 5
<211> LENGTH: 10
<212> TYPE: PRT
<213> ORGANISM: Artificial Sequence
<220> FEATURE:
<223> OTHER INFORMATION: Synthetic Construct
```

<400> SEQUENCE: 5

Ala Arg Ser Tyr Tyr Tyr Gly Met Asp Val
1               5                   10

<210> SEQ ID NO 6
<211> LENGTH: 219
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (33)..(33)
<223> OTHER INFORMATION: X=N,A,Q

<400> SEQUENCE: 6

Asp Ile Val Met Thr Gln Thr Pro Leu Ser Ser Pro Val Thr Leu Gly
1               5                   10                  15

Gln Pro Ala Ser Ile Ser Cys Arg Ser Ser Gln Ser Leu Val His Arg
            20                  25                  30

Xaa Gly Asn Thr Tyr Leu Ser Trp Leu Gln Gln Arg Pro Gly Gln Pro
        35                  40                  45

Pro Arg Leu Leu Ile Tyr Lys Ile Ser Asn Arg Phe Ser Gly Val Pro
    50                  55                  60

Asp Arg Phe Ser Gly Ser Gly Ala Gly Thr Asp Phe Thr Leu Lys Ile
65                  70                  75                  80

Ser Arg Val Glu Ala Glu Asp Val Gly Val Tyr Tyr Cys Met Gln Ala
                85                  90                  95

Arg Gln Phe Pro Leu Thr Phe Gly Gly Gly Thr Lys Val Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215

<210> SEQ ID NO 7
<211> LENGTH: 16
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (10)..(10)
<223> OTHER INFORMATION: X=N,A,Q

<400> SEQUENCE: 7

Arg Ser Ser Gln Ser Leu Val His Arg Xaa Gly Asn Thr Tyr Leu Ser
1               5                   10                  15

```
<210> SEQ ID NO 8
<211> LENGTH: 8
<212> TYPE: PRT
<213> ORGANISM: Artificial Sequence
<220> FEATURE:
<223> OTHER INFORMATION: Synthetic Construct

<400> SEQUENCE: 8

Tyr Lys Ile Ser Asn Arg Phe Ser
1               5

<210> SEQ ID NO 9
<211> LENGTH: 9
<212> TYPE: PRT
<213> ORGANISM: Artificial Sequence
<220> FEATURE:
<223> OTHER INFORMATION: Synthetic Construct

<400> SEQUENCE: 9

Met Gln Ala Arg Gln Phe Pro Leu Thr
1               5

<210> SEQ ID NO 10
<211> LENGTH: 117
<212> TYPE: PRT
<213> ORGANISM: Artificial Sequence
<220> FEATURE:
<223> OTHER INFORMATION: Synthetic Construct

<400> SEQUENCE: 10

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Gly Val
            20                  25                  30

Ser Ile Asn Trp Val Arg Gln Ala Pro Gly Lys Gly Leu Glu Trp Val
        35                  40                  45

Ser Ser Glu Thr Thr Ser Ser Gly Thr Ile Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Ser Tyr Tyr Tyr Gly Met Asp Val Trp Gly Gln Gly Thr Thr
            100                 105                 110

Val Thr Val Ser Ser
        115

<210> SEQ ID NO 11
<211> LENGTH: 112
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (33)..(33)
<223> OTHER INFORMATION: X=N,A,Q

<400> SEQUENCE: 11

Asp Ile Val Met Thr Gln Thr Pro Leu Ser Ser Pro Val Thr Leu Gly
1               5                   10                  15

Gln Pro Ala Ser Ile Ser Cys Arg Ser Ser Gln Ser Leu Val His Arg
            20                  25                  30
```

Xaa Gly Asn Thr Tyr Leu Ser Trp Leu Gln Gln Arg Pro Gly Gln Pro
         35                  40                  45

Pro Arg Leu Leu Ile Tyr Lys Ile Ser Asn Arg Phe Ser Gly Val Pro
 50                  55                  60

Asp Arg Phe Ser Gly Ser Gly Ala Gly Thr Asp Phe Thr Leu Lys Ile
 65                  70                  75                  80

Ser Arg Val Glu Ala Glu Asp Val Gly Val Tyr Tyr Cys Met Gln Ala
                 85                  90                  95

Arg Gln Phe Pro Leu Thr Phe Gly Gly Gly Thr Lys Val Glu Ile Lys
            100                 105                 110

<210> SEQ ID NO 12
<211> LENGTH: 657
<212> TYPE: DNA
<213> ORGANISM: Artificial Sequence
<220> FEATURE:
<223> OTHER INFORMATION: Synthetic Construct

<400> SEQUENCE: 12
gatattgtga tgacccagac tccactctcc tcacctgtca cccttggaca gccggcctcc      60
atctcctgca ggtctagtca agtctcgta cacagagctg aaacaccta cttgagttgg      120 cttcagcaga ggccaggcca gcctccaaga ctcctaattt ataagatttc taaccggttc     180
tctggggtcc cagacagatt cagtggcagt ggggcaggga cagatttcac actgaaaatc     240
agcagggtgg aagctgagga tgtcggagtt tattattgca tgcaagctag acaatttccg     300 ctcacttttcg gcggagggac caaggtggag atcaaacgga ccgtggctgc accatctgtc     360
ttcatcttcc cgccatctga tgagcagttg aaatctggaa ctgcctctgt tgtgtgcctg     420
ctgaataact tctatcccag agaggccaaa gtacagtgga aggtggataa cgccctccaa     480
tcgggtaact cccaggagag tgtcacagag caggacagca aggacagcac ctacagcctc     540
agcagcaccc tgacgctgag caaagcagac tacgagaaac acaaagtcta cgcctgcgaa     600
gtcacccatc agggcctgag ctcgcccgtc acaaagagct tcaacagggg agagtgc      657

<210> SEQ ID NO 13
<211> LENGTH: 1329
<212> TYPE: DNA
<213> ORGANISM: Artificial Sequence
<220> FEATURE:
<223> OTHER INFORMATION: Synthetic Construct

<400> SEQUENCE: 13
gaggtgcagc tggtggagtc tggaggaggc ctggtcaagc ctgggggtc cctgagactc      60 tcctgtgcag cctctggatt caccttcagt ggcgtcagca taaactgggt ccgccaggct     120
ccagggaagg ggctggagtg ggtctcatcc gagactacaa gtagtggtac aatatactac     180
gcagactcag tgaagggccg attcaccatc tccagagaca acgccaagaa ctcactgtat     240
ctgcaaatga acagcctgag agccgaggac acggctgtgt attactgtgc gagaagctac     300
tactacggta tggacgtctg gggccaaggg accacggtca ccgtctcctc agcctccacc     360
aagggcccat cggtcttccc gctagcgccc tgctccagga gcacctccga gagcacagcc     420
gccctgggct gcctggtcaa ggactacttc cccgaaccgg tgacggtgtc gtggaactca     480
ggcgccctga ccagcggcgt gcacaccttc ccggctgtcc tacagtcctc aggactctac     540
tccctcagca gcgtggtgac cgtgccctcc agcagcttgg gcacgaagac ctacacctgc     600
aacgtagatc acaagcccag caacaccaag gtggacaaga gagttgagtc caaatatggt     660

| | |
|---|---|
| cccccatgcc caccctgccc agcacctgag gccgccgggg gaccatcagt cttcctgttc | 720 |
| cccccaaaac ccaaggacac tctcatgatc tcccggaccc ctgaggtcac gtgcgtggtg | 780 |
| gtggacgtga gccaggaaga ccccgaggtc cagttcaact ggtacgtgga tggcgtggag | 840 |
| gtgcataatg ccaagacaaa gccgcgggag gagcagttca acagcacgta ccgtgtggtc | 900 |
| agcgtcctca ccgtcctgca ccaggactgg ctgaacggca aggagtacaa gtgcaaggtc | 960 |
| tccaacaaag gcctcccgtc ctccatcgag aaaaccatct ccaaagccaa agggcagccc | 1020 |
| cgagagccac aggtgtacac cctgccccca tcccaggagg agatgaccaa gaaccaggtc | 1080 |
| agcctgacct gcctggtcaa aggcttctac cccagcgaca tcgccgtgga gtgggaaagc | 1140 |
| aatgggcagc cggagaacaa ctacaagacc acgcctcccg tgctggactc cgacggctcc | 1200 |
| ttcttcctct acagcaggct aaccgtggac aagagcaggt ggcaggaggg gaatgtcttc | 1260 |
| tcatgctccg tgatgcatga ggctctgcac aaccactaca cacagaagag cctctccctg | 1320 |
| tctctgggt | 1329 |

<210> SEQ ID NO 14
<211> LENGTH: 657
<212> TYPE: DNA
<213> ORGANISM: Artificial Sequence
<220> FEATURE:
<223> OTHER INFORMATION: Synthetic Construct

<400> SEQUENCE: 14

| | |
|---|---|
| gacatcgtga tgacccagac ccctttatcc tcccccgtta cactgggcca gccgcttcc | 60 |
| atctcttgtc gttcctccca gtctttagtg catcgtgctg caacaccta tttatcttgg | 120 |
| ctgcagcaga ggcccggtca gcctcctcgt ctgctgatct acaagatcag caaccggttc | 180 |
| tccggcgtgc ccgatcgttt ttccggctcc ggagccggca ccgatttcac tttaaagatc | 240 |
| tctcgtgtgg aggccgagga tgtgggcgtg tactactgca tgcaagctcg tcagttccct | 300 |
| ctgaccttcg gcggcggcac caaggtggag atcaagcgta cggtggctgc accatctgtc | 360 |
| ttcatcttcc cgccatctga tgagcagttg aaatctggaa ctgcctctgt tgtgtgcctg | 420 |
| ctgaataact tctatcccag agaggccaaa gtacagtgga aggtggataa cgccctccaa | 480 |
| tcgggtaact cccaggagag tgtcacagag caggacagca aggacagcac ctacagcctc | 540 |
| agcagcaccc tgacgctgag caaagcagac tacgagaaac acaaagtcta cgcctgcgaa | 600 |
| gtcacccatc agggcctgag ctcgcccgtc acaaagagct tcaacagggg agagtgt | 657 |

<210> SEQ ID NO 15
<211> LENGTH: 1329
<212> TYPE: DNA
<213> ORGANISM: Artificial Sequence
<220> FEATURE:
<223> OTHER INFORMATION: Synthetic Construct

<400> SEQUENCE: 15

| | |
|---|---|
| gaggtgcagc tcgtggagtc cggcggagga ctggtgaagc ccggtggctc tttaaggctg | 60 |
| tcttgtgccg cttccggctt caccttctcc ggcgtgtcca tcaactgggt gaggcaagct | 120 |
| cccggtaagg gtttagagtg ggtgtcctcc gagaccacct cctccggcac catctactac | 180 |
| gccgactccg tgaagggccg gttcaccatc tctcgtgaca cgccaagaa ctctttatat | 240 |
| ttacagatga actctttaag ggccgaggac accgccgtgt actactgcgc tcgttcctac | 300 |
| tactacggca tggacgtgtg gggccaaggt accaccgtga cagtctcctc cgctagcacc | 360 |
| aagggcccat ccgtcttccc cctggcgccc tgctccagga gcacctccga gagcacagcc | 420 |

```
gccctgggct gcctggtcaa ggactacttc cccgaaccgg tgacggtgtc gtggaactca    480
ggcgccctga ccagcggcgt gcacaccttc ccggctgtcc tacagtcctc aggactctac    540
tccctcagca gcgtggtgac cgtgccctcc agcagcttgg gcacgaagac ctacacctgc    600
aacgtagatc acaagcccag caacaccaag gtggacaaga gagttgagtc caaatatggt    660
cccccatgcc caccatgccc agcacctgag gcagctgggg gaccatcagt cttcctgttc    720
cccccaaaac ccaaggacac tctcatgatc tcccggaccc ctgaggtcac gtgcgtggtg    780
gtggacgtga gccaggaaga ccccgaggtc cagttcaact ggtacgtgga tggcgtggag    840
gtgcataatg ccaagacaaa gccgcgggag gagcagttca acagcacgta ccgtgtggtc    900
agcgtcctca ccgtcctgca ccaggactgg ctgaacggca aggagtacaa gtgcaaggtc    960
tccaacaaag gcctcccgtc ctccatcgag aaaaccatct ccaaagccaa agggcagccc   1020
cgagagccac aggtgtacac cctgccccca tcccaggagg agatgaccaa gaaccaggtc   1080
agcctgacct gcctggtcaa aggcttctac cccagcgaca tcgccgtgga gtgggagagc   1140
aatgggcagc cggagaacaa ctacaagacc acgcctcccg tgctggactc cgacggctcc   1200
ttcttcctct acagcaggct aaccgtggac aagagcaggt ggcaggaggg gaatgtcttc   1260
tcatgctccg tgatgcatga ggctctgcac aaccactaca cacagaagag cctctccctg   1320
tctctgggt                                                           1329

<210> SEQ ID NO 16
<211> LENGTH: 657
<212> TYPE: DNA
<213> ORGANISM: Artificial Sequence
<220> FEATURE:
<223> OTHER INFORMATION: Synthetic Construct

<400> SEQUENCE: 16
gacatcgtga tgacccagac ccctttatcc tcccccgtta cactgggcca gcccgcttcc     60
atcagctgta ggtcctccca gtctttagtg catcgtcaag gtaacacata tttatcttgg    120
ctgcagcaga ggcccggtca acctcctcgg ctgctgatct acaagatctc caaccggttc    180
tccggcgtgc ccgataggtt ctccggctcc ggcgctggca ccgatttcac tttaaagatc    240
tctcgtgtgg aggctgagga tgtgggcgtg tactactgca tgcaagctcg tcagttccct    300
ttaaccttcg gaggcggcac caaggtggag atcaagcgta cggtggctgc accatctgtc    360
ttcatcttcc cgccatctga tgagcagttg aaatctggaa ctgcctctgt tgtgtgcctg    420
ctgaataact tctatcccag agaggccaaa gtacagtgga aggtggataa cgccctccaa    480
tcgggtaact cccaggagag tgtcacagag caggacagca aggacagcac ctacagcctc    540
agcagcaccc tgacgctgag caaagcagac tacgagaaac acaaagtcta cgcctgcgaa    600
gtcacccatc agggcctgag ctcgcccgtc acaaagagct tcaacagggg agagtgt       657

<210> SEQ ID NO 17
<211> LENGTH: 657
<212> TYPE: DNA
<213> ORGANISM: Artificial Sequence
<220> FEATURE:
<223> OTHER INFORMATION: Synthetic Construct

<400> SEQUENCE: 17
gacatcgtga tgacccagac ccctttatcc tcccccgtta cactgggcca gcccgcttcc     60
atctcttgtc gttcctccca gtctttagtg catcgtgctg gcaacaccta tttatcttgg    120
```

| | |
|---|---|
| ctgcagcaga ggcccggtca gcctcctcgt ctgctgatct acaagatcag caaccggttc | 180 |
| tccggcgtgc ccgatcgttt tccggctcc ggagccggca ccgatttcac tttaaagatc | 240 |
| tctcgtgtgg aggccgagga tgtgggcgtg tactactgca tgcaagctcg tcagttccct | 300 |
| ctgaccttcg gcggcggcac caaggtggag atcaagcgta cggtggctgc accatctgtc | 360 |
| ttcatcttcc cgccatctga tgagcagttg aaatctggaa ctgcctctgt tgtgtgcctg | 420 |
| ctgaataact tctatcccag agaggccaaa gtacagtgga aggtggataa cgccctccaa | 480 |
| tcgggtaact cccaggagag tgtcacagag caggacagca aggacagcac ctacagcctc | 540 |
| agcagcaccc tgacgctgag caaagcagac tacgagaaac acaaagtcta cgcctgcgaa | 600 |
| gtcacccatc agggcctgag ctcgcccgtc acaaagagct tcaacagggg agagtgt | 657 |

<210> SEQ ID NO 18
<211> LENGTH: 657
<212> TYPE: DNA
<213> ORGANISM: Artificial Sequence
<220> FEATURE:
<223> OTHER INFORMATION: Synthetic Construct

<400> SEQUENCE: 18

| | |
|---|---|
| gacatcgtga tgacccagac ccctttatcc tcccccgtta cactgggcca gcccgcttcc | 60 |
| atcagctgta ggtcctccca gtctttagtg catcgtcaag gtaacacata tttatcttgg | 120 |
| ctgcagcaga ggcccggtca acctcctcgg ctgctgatct acaagatctc caaccggttc | 180 |
| tccggcgtgc ccgataggtt ctccggctcc ggcgctggca ccgatttcac tttaaagatc | 240 |
| tctcgtgtgg aggctgagga tgtgggcgtg tactactgca tgcaagctcg tcagttccct | 300 |
| ttaaccttcg gaggcggcac caaggtggag atcaagcgta cggtggctgc accatctgtc | 360 |
| ttcatcttcc cgccatctga tgagcagttg aaatctggaa ctgcctctgt tgtgtgcctg | 420 |
| ctgaataact tctatcccag agaggccaaa gtacagtgga aggtggataa cgccctccaa | 480 |
| tcgggtaact cccaggagag tgtcacagag caggacagca aggacagcac ctacagcctc | 540 |
| agcagcaccc tgacgctgag caaagcagac tacgagaaac acaaagtcta cgcctgcgaa | 600 |
| gtcacccatc agggcctgag ctcgcccgtc acaaagagct tcaacagggg agagtgt | 657 |

<210> SEQ ID NO 19
<211> LENGTH: 1341
<212> TYPE: DNA
<213> ORGANISM: Artificial Sequence
<220> FEATURE:
<223> OTHER INFORMATION: Synthetic Construct

<400> SEQUENCE: 19

| | |
|---|---|
| gaggtgcagc tcgtggagtc cggcggagga ctggtgaagc ccgtggctc tttaaggctg | 60 |
| tcttgtgccg cttccggctt caccttctcc ggcgtgtcca tcaactgggt gaggcaagct | 120 |
| cccggtaagg gtttagagtg ggtgtcctcc gagaccacct cctccggcac catctactac | 180 |
| gccgactccg tgaagggccg gttcaccatc tctcgtgaca cgccaagaa ctctttatat | 240 |
| ttacagatga actctttaag ggccgaggac accgccgtgt actactgcgc tcgttcctac | 300 |
| tactacggca tggacgtgtg gggccaaggt accaccgtga cagtctcctc cgctagcacc | 360 |
| aagggcccat cggtcttccc cctggcaccc tcctccaaga gcacctctgg gggcacagcg | 420 |
| gccctgggct gcctggtcaa ggactacttc cccgaaccgg tgacggtgtc gtggaactca | 480 |
| ggcgccctga ccagcggcgt gcacaccttc ccggccgtcc tacagtcctc aggactctac | 540 |
| tccctcagca gcgtggtgac cgtgccctcc agcagcttgg gcacccagac ctacatctgc | 600 |

-continued

```
aacgtgaatc acaagcccag caacaccaag gtggacaagc gggttgagcc caaatcttgt    660
gacaaaactc acacatgccc accgtgccca gcacctgaag ccgaggggc accgtcagtc    720 ttcctcttcc ccccaaaacc caaggacacc ctcatgatct cccggacccc tgaggtcaca    780
tgcgtggtgg tggacgtgag ccacgaagac cctgaggtca agttcaactg gtacgtggac    840
ggcgtggagg tgcataatgc caagacaaag ccgcgggagg agcagtacaa cagcacgtac    900
cgtgtggtca gcgtcctcac cgtcctgcac caggactggc tgaatggcaa ggagtacaag    960
tgcaaggtct ccaacaaagc cctcccatcc tccatcgaga aaaccatctc caaagccaaa   1020
gggcagcccc gagaaccaca ggtgtacacc ctgcccccat cccgggagga tgaccaag    1080 aaccaggtca gcctgacctg cctggtcaaa ggcttctatc ccagcgacat cgccgtggag   1140
tgggagagca tgggcagcc ggagaacaac tacaagacca cgcctcccgt gctggactcc   1200
gacggctcct tcttcctcta cagcaagctc accgtggaca agagcaggtg gcagcagggg   1260
aacgtcttct catgctccgt gatgcatgag gctctgcaca accactacac gcagaagagc   1320
ctctccctgt ctccgggtaa a                                              1341
```

<210> SEQ ID NO 20
<211> LENGTH: 390
<212> TYPE: PRT
<213> ORGANISM: Artificial Sequence
<220> FEATURE:
<223> OTHER INFORMATION: Synthetic Construct

<400> SEQUENCE: 20

```
His His His His His His His His Ala Ala Pro Cys Pro Asp Ala Cys
1               5                   10                  15

Cys Pro His Gly Ser Ser Gly Leu Arg Cys Thr Arg Asp Gly Ala Leu
            20                  25                  30

Asp Ser Leu His His Leu Pro Gly Ala Glu Asn Leu Thr Glu Leu Tyr
        35                  40                  45

Ile Glu Asn Gln Gln His Leu Gln His Leu Glu Leu Arg Asp Leu Arg
    50                  55                  60

Gly Leu Gly Glu Leu Arg Asn Leu Thr Ile Val Lys Ser Gly Leu Arg
65                  70                  75                  80

Phe Val Ala Pro Asp Ala Phe His Phe Thr Pro Arg Leu Ser Arg Leu
                85                  90                  95

Asn Leu Ser Phe Asn Ala Leu Glu Ser Leu Ser Trp Lys Thr Val Gln
            100                 105                 110

Gly Leu Ser Leu Gln Glu Leu Val Leu Ser Gly Asn Pro Leu His Cys
        115                 120                 125

Ser Cys Ala Leu Arg Trp Leu Gln Arg Trp Glu Glu Gly Leu Gly
    130                 135                 140

Gly Val Pro Glu Gln Lys Leu Gln Cys His Gly Gln Gly Pro Leu Ala
145                 150                 155                 160

His Met Pro Asn Ala Ser Cys Gly Val Pro Thr Leu Lys Val Gln Val
                165                 170                 175

Pro Asn Ala Ser Val Asp Val Gly Asp Asp Val Leu Leu Arg Cys Gln
            180                 185                 190

Val Glu Gly Arg Gly Leu Glu Gln Ala Gly Trp Ile Leu Thr Glu Leu
        195                 200                 205

Glu Gln Ser Ala Thr Val Met Lys Ser Gly Gly Leu Pro Ser Leu Gly
    210                 215                 220
```

```
Leu Thr Leu Ala Asn Val Thr Ser Asp Leu Asn Arg Lys Asn Val Thr
225                 230                 235                 240

Cys Trp Ala Glu Asn Asp Val Gly Arg Ala Glu Val Ser Val Gln Val
            245                 250                 255

Asn Val Ser Phe Pro Ala Ser Val Gln Leu His Thr Ala Val Glu Met
        260                 265                 270

His His Trp Cys Ile Pro Phe Ser Val Asp Gly Gln Pro Ala Pro Ser
    275                 280                 285

Leu Arg Trp Leu Phe Asn Gly Ser Val Leu Asn Glu Thr Ser Phe Ile
290                 295                 300

Phe Thr Glu Phe Leu Glu Pro Ala Ala Asn Glu Thr Val Arg His Gly
305                 310                 315                 320

Cys Leu Arg Leu Asn Gln Pro Thr His Val Asn Asn Gly Asn Tyr Thr
            325                 330                 335

Leu Leu Ala Ala Asn Pro Phe Gly Gln Ala Ser Ala Ser Ile Met Ala
        340                 345                 350

Ala Phe Met Asp Asn Pro Phe Glu Phe Asn Pro Glu Asp Pro Ile Pro
    355                 360                 365

Val Ser Phe Ser Pro Val Asp Thr Asn Ser Thr Ser Gly Asp Pro Val
370                 375                 380

Glu Lys Lys Asp Glu Thr
385                 390

<210> SEQ ID NO 21
<211> LENGTH: 384
<212> TYPE: PRT
<213> ORGANISM: Artificial Sequence
<220> FEATURE:
<223> OTHER INFORMATION: Synthetic Construct

<400> SEQUENCE: 21

His His His His His His His Ala Ala Pro Cys Pro Asp Ala Cys
1               5                   10                  15

Cys Pro His Gly Ser Ser Gly Leu Arg Cys Thr Arg Asp Gly Ala Leu
            20                  25                  30

Asp Ser Leu His His Leu Pro Gly Ala Glu Asn Leu Thr Glu Leu Tyr
        35                  40                  45

Ile Glu Asn Gln Gln His Leu Gln His Leu Glu Leu Arg Asp Leu Arg
    50                  55                  60

Gly Leu Gly Glu Leu Arg Asn Leu Thr Ile Val Lys Ser Gly Leu Arg
65                  70                  75                  80

Phe Val Ala Pro Asp Ala Phe His Phe Thr Pro Arg Leu Ser Arg Leu
                85                  90                  95

Asn Leu Ser Phe Asn Ala Leu Glu Ser Leu Ser Trp Lys Thr Val Gln
            100                 105                 110

Gly Leu Ser Leu Gln Glu Leu Val Leu Ser Gly Asn Pro Leu His Cys
        115                 120                 125

Ser Cys Ala Leu Arg Trp Leu Gln Arg Trp Glu Glu Glu Gly Leu Gly
    130                 135                 140

Gly Val Pro Glu Gln Lys Leu Gln Cys His Gly Gln Gly Pro Leu Ala
145                 150                 155                 160

His Met Pro Asn Ala Ser Cys Gly Val Pro Thr Leu Lys Val Gln Val
                165                 170                 175

Pro Asn Ala Ser Val Asp Val Gly Asp Asp Val Leu Leu Arg Cys Gln
            180                 185                 190
```

-continued

```
Val Glu Gly Arg Gly Leu Glu Gln Ala Gly Trp Ile Leu Thr Glu Leu
        195                 200                 205

Glu Gln Ser Ala Thr Val Met Lys Ser Gly Gly Leu Pro Ser Leu Gly
    210                 215                 220

Leu Thr Leu Ala Asn Val Thr Ser Asp Leu Asn Arg Lys Asn Val Thr
225                 230                 235                 240

Cys Trp Ala Glu Asn Asp Val Gly Arg Ala Glu Val Ser Val Gln Val
                245                 250                 255

Asn Val Ser Phe Pro Ala Ser Val Gln Leu His Thr Ala Val Glu Met
            260                 265                 270

His His Trp Cys Ile Pro Phe Ser Val Asp Gly Gln Pro Ala Pro Ser
        275                 280                 285

Leu Arg Trp Leu Phe Asn Gly Ser Val Leu Asn Glu Thr Ser Phe Ile
    290                 295                 300

Phe Thr Glu Phe Leu Glu Pro Ala Ala Asn Glu Thr Val Arg His Gly
305                 310                 315                 320

Cys Leu Arg Leu Asn Gln Pro Thr His Val Asn Asn Gly Asn Tyr Thr
                325                 330                 335

Leu Leu Ala Ala Asn Pro Phe Gly Gln Ala Ser Ala Ser Ile Met Ala
            340                 345                 350

Ala Phe Met Asp Asn Pro Phe Glu Phe Asn Pro Glu Asp Pro Ile Pro
        355                 360                 365

Asp Thr Asn Ser Thr Ser Gly Asp Pro Val Glu Lys Lys Asp Glu Thr
    370                 375                 380
```

<210> SEQ ID NO 22
<211> LENGTH: 407
<212> TYPE: PRT
<213> ORGANISM: Artificial Sequence
<220> FEATURE:
<223> OTHER INFORMATION: Synthetic Construct

<400> SEQUENCE: 22

```
His His His His His His His Cys Pro Thr Ser Cys Lys Cys Ser
1               5                   10                  15

Ala Ser Arg Ile Trp Cys Ser Asp Pro Ser Pro Gly Ile Val Ala Phe
            20                  25                  30

Pro Arg Leu Glu Pro Asn Ser Val Asp Pro Glu Asn Ile Thr Glu Ile
        35                  40                  45

Phe Ile Ala Asn Gln Lys Arg Leu Glu Ile Ile Asn Glu Asp Asp Val
    50                  55                  60

Glu Ala Tyr Val Gly Leu Arg Asn Leu Thr Ile Val Asp Ser Gly Leu
65                  70                  75                  80

Lys Phe Val Ala His Lys Ala Phe Leu Lys Asn Ser Asn Leu Gln His
                85                  90                  95

Ile Asn Phe Thr Arg Asn Lys Leu Thr Ser Leu Ser Arg Lys His Phe
            100                 105                 110

Arg His Leu Asp Leu Ser Glu Leu Ile Leu Val Gly Asn Pro Phe Thr
        115                 120                 125

Cys Ser Cys Asp Ile Met Trp Ile Lys Thr Leu Gln Glu Ala Lys Ser
    130                 135                 140

Ser Pro Asp Thr Gln Asp Leu Tyr Cys Leu Asn Glu Ser Ser Lys Asn
145                 150                 155                 160

Ile Pro Leu Ala Asn Leu Gln Ile Pro Asn Cys Gly Leu Pro Ser Ala
                165                 170                 175
```

```
Asn Leu Ala Ala Pro Asn Leu Thr Val Glu Glu Gly Lys Ser Ile Thr
                180                 185                 190
Leu Ser Cys Ser Val Ala Gly Asp Pro Val Pro Asn Met Tyr Trp Asp
            195                 200                 205
Val Gly Asn Leu Val Ser Lys His Met Asn Glu Thr Ser His Thr Gln
        210                 215                 220
Gly Ser Leu Arg Ile Thr Asn Ile Ser Ser Asp Ser Gly Lys Gln
225                 230                 235                 240
Ile Ser Cys Val Ala Glu Asn Leu Val Gly Asp Gln Asp Ser Val
                245                 250                 255
Asn Leu Thr Val His Phe Ala Pro Thr Ile Thr Phe Leu Glu Ser Pro
            260                 265                 270
Thr Ser Asp His His Trp Cys Ile Pro Phe Thr Val Lys Gly Asn Pro
        275                 280                 285
Lys Pro Ala Leu Gln Trp Phe Tyr Asn Gly Ala Ile Leu Asn Glu Ser
290                 295                 300
Lys Tyr Ile Cys Thr Lys Ile His Val Thr Asn His Thr Glu Tyr His
305                 310                 315                 320
Gly Cys Leu Gln Leu Asp Asn Pro Thr His Met Asn Asn Gly Asp Tyr
                325                 330                 335
Thr Leu Ile Ala Lys Asn Glu Tyr Gly Lys Asp Glu Lys Gln Ile Ser
            340                 345                 350
Ala His Phe Met Gly Trp Pro Gly Ile Asp Asp Gly Ala Asn Pro Asn
        355                 360                 365
Tyr Pro Asp Val Ile Tyr Glu Asp Tyr Gly Thr Ala Ala Asn Asp Ile
    370                 375                 380
Gly Asp Thr Thr Asn Arg Ser Asn Glu Ile Pro Ser Thr Asp Val Thr
385                 390                 395                 400
Asp Lys Thr Gly Arg Glu His
                405

<210> SEQ ID NO 23
<211> LENGTH: 405
<212> TYPE: PRT
<213> ORGANISM: Artificial Sequence
<220> FEATURE:
<223> OTHER INFORMATION: Synthetic Construct

<400> SEQUENCE: 23

His His His His His His His Cys Pro Ala Asn Cys Val Cys Ser
1               5                   10                  15
Lys Thr Glu Ile Asn Cys Arg Arg Pro Asp Asp Gly Asn Leu Phe Pro
            20                  25                  30
Leu Leu Glu Gly Gln Asp Ser Gly Asn Ser Asn Gly Asn Ala Ser Ile
        35                  40                  45
Asn Ile Thr Asp Ile Ser Arg Asn Ile Thr Ser Ile His Ile Glu Asn
    50                  55                  60
Trp Arg Ser Leu His Thr Leu Asn Ala Val Asp Met Glu Leu Tyr Thr
65                  70                  75                  80
Gly Leu Gln Lys Leu Thr Ile Lys Asn Ser Gly Leu Arg Ser Ile Gln
                85                  90                  95
Pro Arg Ala Phe Ala Lys Asn Pro His Leu Arg Tyr Ile Asn Leu Ser
            100                 105                 110
Ser Asn Arg Leu Thr Thr Leu Ser Trp Gln Leu Phe Gln Thr Leu Ser
        115                 120                 125
```

Leu Arg Glu Leu Gln Leu Glu Gln Asn Phe Phe Asn Cys Ser Cys Asp
130                 135                 140

Ile Arg Trp Met Gln Leu Trp Gln Glu Gln Gly Glu Ala Lys Leu Asn
145                 150                 155                 160

Ser Gln Asn Leu Tyr Cys Ile Asn Ala Asp Gly Ser Gln Leu Pro Leu
                165                 170                 175

Phe Arg Met Asn Ile Ser Gln Cys Asp Leu Pro Glu Ile Ser Val Ser
            180                 185                 190

His Val Asn Leu Thr Val Arg Glu Gly Asp Asn Ala Val Ile Thr Cys
        195                 200                 205

Asn Gly Ser Gly Ser Pro Leu Pro Asp Val Asp Trp Ile Val Thr Gly
210                 215                 220

Leu Gln Ser Ile Asn Thr His Gln Thr Asn Leu Asn Trp Thr Asn Val
225                 230                 235                 240

His Ala Ile Asn Leu Thr Leu Val Asn Val Thr Ser Glu Asp Asn Gly
                245                 250                 255

Phe Thr Leu Thr Cys Ile Ala Glu Asn Val Val Gly Met Ser Asn Ala
            260                 265                 270

Ser Val Ala Leu Thr Val Tyr Tyr Pro Pro Arg Val Val Ser Leu Glu
        275                 280                 285

Glu Pro Glu Leu Arg Leu Glu His Cys Ile Glu Phe Val Val Arg Gly
290                 295                 300

Asn Pro Pro Pro Thr Leu His Trp Leu His Asn Gly Gln Pro Leu Arg
305                 310                 315                 320

Glu Ser Lys Ile Ile His Val Glu Tyr Tyr Gln Glu Gly Glu Ile Ser
                325                 330                 335

Glu Gly Cys Leu Leu Phe Asn Lys Pro Thr His Tyr Asn Asn Gly Asn
            340                 345                 350

Tyr Thr Leu Ile Ala Lys Asn Pro Leu Gly Thr Ala Asn Gln Thr Ile
        355                 360                 365

Asn Gly His Phe Leu Lys Glu Pro Phe Pro Glu Ser Thr Asp Asn Phe
370                 375                 380

Ile Leu Phe Asp Glu Val Ser Pro Thr Pro Ile Thr Val Thr His
385                 390                 395                 400

Lys Pro Glu Glu Asp
            405

<210> SEQ ID NO 24
<211> LENGTH: 384
<212> TYPE: PRT
<213> ORGANISM: Artificial Sequence
<220> FEATURE:
<223> OTHER INFORMATION: Synthetic Construct

<400> SEQUENCE: 24

His His His His His His His Ala Ser Pro Cys Pro Asp Ala Cys
1               5                   10                  15

Cys Pro His Gly Ser Ser Gly Leu Arg Cys Thr Arg Asp Gly Ala Leu
            20                  25                  30

Asp Ser Leu His His Leu Pro Gly Ala Glu Asn Leu Thr Glu Leu Tyr
        35                  40                  45

Ile Glu Asn Gln Gln His Leu Gln His Leu Glu Leu Arg Asp Leu Arg
    50                  55                  60

Gly Leu Gly Glu Leu Arg Asn Leu Thr Ile Val Lys Ser Gly Leu Arg
65                  70                  75                  80

```
Phe Val Ala Pro Asp Ala Phe His Phe Thr Pro Arg Leu Ser Arg Leu
                85                  90                  95

Asn Leu Ser Phe Asn Ala Leu Glu Ser Leu Ser Trp Lys Thr Val Gln
            100                 105                 110

Gly Leu Ser Leu Gln Glu Leu Val Leu Ser Gly Asn Pro Leu His Cys
            115                 120                 125

Ser Cys Ala Leu Arg Trp Leu Gln Arg Trp Glu Glu Glu Gly Leu Gly
130                 135                 140

Gly Val His Glu Gln Lys Leu Gln Cys His Gly Gln Gly Pro Leu Ala
145                 150                 155                 160

His Met Pro Asn Ala Ser Cys Gly Val Pro Met Leu Lys Val Gln Val
                165                 170                 175

Pro Asn Ala Ser Val Asp Val Gly Asp Asp Val Leu Leu Trp Cys Gln
            180                 185                 190

Val Glu Gly Arg Gly Leu Glu Gln Ala Gly Trp Ile Leu Thr Glu Leu
            195                 200                 205

Glu Gln Ser Ala Thr Val Met Lys Ser Gly Ala Leu Pro Ser Leu Gly
210                 215                 220

Leu Thr Leu Ala Asn Val Thr Ser Asp Leu Asn Arg Lys Asn Val Thr
225                 230                 235                 240

Cys Trp Ala Glu Asn Asp Val Gly Arg Ala Glu Leu Ser Val Gln Val
                245                 250                 255

Asn Val Ser Phe Pro Ala Ser Val Gln Leu His Thr Ala Val Glu Met
            260                 265                 270

His His Trp Cys Ile Pro Phe Ser Val Asp Gly Gln Pro Ala Pro Ser
            275                 280                 285

Leu Arg Trp Leu Phe Asn Gly Ser Val Leu Asn Glu Thr Ser Phe Ile
290                 295                 300

Phe Thr Glu Phe Leu Glu Pro Ala Ala Asn Glu Thr Val Arg His Gly
305                 310                 315                 320

Cys Leu Arg Leu Asn Gln Pro Thr His Val Asn Asn Gly Asn Tyr Thr
                325                 330                 335

Leu Leu Ala Ala Asn Pro Phe Gly Gln Ala Ser Ala Ser Ile Met Ala
            340                 345                 350

Ala Phe Met Asp Asn Pro Phe Glu Phe Asn Pro Glu Asp Pro Ile Pro
            355                 360                 365

Asp Thr Asn Ser Thr Ser Gly Asp Pro Val Glu Lys Lys Asp Glu Thr
370                 375                 380

<210> SEQ ID NO 25
<211> LENGTH: 387
<212> TYPE: PRT
<213> ORGANISM: Artificial Sequence
<220> FEATURE:
<223> OTHER INFORMATION: Synthetic Construct

<400> SEQUENCE: 25

His His His His His His His Ala Ala Ser Cys Arg Glu Val Cys
1               5                   10                  15

Cys Pro Val Gly Pro Ser Gly Leu Arg Cys Thr Arg Ala Gly Ser Leu
            20                  25                  30

Asp Thr Leu Arg Gly Leu Arg Gly Ala Gly Asn Leu Thr Glu Leu Tyr
            35                  40                  45

Val Glu Asn Gln Gln His Leu Gln Arg Leu Glu Phe Glu Asp Leu Gln
50                  55                  60
```

```
Gly Leu Gly Glu Leu Arg Ser Leu Thr Ile Val Lys Ser Gly Leu Arg
 65                  70                  75                  80

Phe Val Ala Pro Asp Ala Phe Arg Phe Thr Pro Arg Leu Ser His Leu
                 85                  90                  95

Asn Leu Ser Ser Asn Ala Leu Glu Ser Leu Ser Trp Lys Thr Val Gln
            100                 105                 110

Gly Leu Ser Leu Gln Asp Leu Thr Leu Ser Gly Asn Pro Leu His Cys
        115                 120                 125

Ser Cys Ala Leu Phe Trp Leu Gln Arg Trp Glu Gln Glu Gly Leu Cys
    130                 135                 140

Gly Val His Thr Gln Thr Leu His Asp Ser Gly Pro Gly Asp Gln Phe
145                 150                 155                 160

Leu Pro Leu Gly His Asn Thr Ser Cys Gly Val Pro Thr Val Lys Ile
                165                 170                 175

Gln Met Pro Asn Asp Ser Val Glu Val Gly Asp Asp Val Phe Leu Gln
            180                 185                 190

Cys Gln Val Glu Gly Leu Ala Leu Gln Gln Ala Asp Trp Ile Leu Thr
        195                 200                 205

Glu Leu Glu Gly Ala Ala Thr Val Lys Lys Phe Gly Asp Leu Pro Ser
    210                 215                 220

Leu Gly Leu Ile Leu Val Asn Val Thr Ser Asp Leu Asn Lys Lys Asn
225                 230                 235                 240

Val Thr Cys Trp Ala Glu Asn Asp Val Gly Arg Ala Glu Val Ser Val
                245                 250                 255

Gln Val Ser Val Ser Phe Pro Ala Ser Val His Leu Gly Leu Ala Val
            260                 265                 270

Glu Gln His His Trp Cys Ile Pro Phe Ser Val Asp Gly Gln Pro Ala
        275                 280                 285

Pro Ser Leu Arg Trp Leu Phe Asn Gly Ser Val Leu Asn Glu Thr Ser
    290                 295                 300

Phe Ile Phe Thr Gln Phe Leu Glu Ser Ala Leu Thr Asn Glu Thr Met
305                 310                 315                 320

Arg His Gly Cys Leu Arg Leu Asn Gln Pro Thr His Val Asn Asn Gly
                325                 330                 335

Asn Tyr Thr Leu Leu Ala Ala Asn Pro Tyr Gly Gln Ala Ala Ala Ser
            340                 345                 350

Val Met Ala Ala Phe Met Asp Asn Pro Phe Glu Phe Asn Pro Glu Asp
        355                 360                 365

Pro Ile Pro Asp Gly Asn Ser Thr Ser Arg Asp Pro Val Glu Lys Lys
    370                 375                 380

Asp Glu Thr
385

<210> SEQ ID NO 26
<211> LENGTH: 387
<212> TYPE: PRT
<213> ORGANISM: Artificial Sequence
<220> FEATURE:
<223> OTHER INFORMATION: Synthetic Construct

<400> SEQUENCE: 26

His His His His His His His Ala Ala Ser Cys Arg Glu Thr Cys
  1               5                  10                  15

Cys Pro Val Gly Pro Ser Gly Leu Arg Cys Thr Arg Ala Gly Thr Leu
                 20                  25                  30
```

Asn Thr Leu Arg Gly Leu Arg Gly Ala Gly Asn Leu Thr Glu Leu Tyr
         35                  40                  45

Val Glu Asn Gln Arg Asp Leu Gln Arg Leu Glu Phe Glu Asp Leu Gln
 50                  55                  60

Gly Leu Gly Glu Leu Arg Ser Leu Thr Ile Val Lys Ser Gly Leu Arg
 65                  70                  75                  80

Phe Val Ala Pro Asp Ala Phe His Phe Thr Pro Arg Leu Ser His Leu
                 85                  90                  95

Asn Leu Ser Ser Asn Ala Leu Glu Ser Leu Ser Trp Lys Thr Val Gln
             100                 105                 110

Gly Leu Ser Leu Gln Asp Leu Thr Leu Ser Gly Asn Pro Leu His Cys
             115                 120                 125

Ser Cys Ala Leu Leu Trp Leu Gln Arg Trp Glu Gln Glu Asp Leu Cys
130                 135                 140

Gly Val Tyr Thr Gln Lys Leu Gln Gly Ser Gly Ser Gly Asp Gln Phe
145                 150                 155                 160

Leu Pro Leu Gly His Asn Asn Ser Cys Gly Val Pro Ser Val Lys Ile
                 165                 170                 175

Gln Met Pro Asn Asp Ser Val Glu Val Gly Asp Val Phe Leu Gln
             180                 185                 190

Cys Gln Val Glu Gly Gln Ala Leu Gln Gln Ala Asp Trp Ile Leu Thr
            195                 200                 205

Glu Leu Glu Gly Thr Ala Thr Met Lys Lys Ser Gly Asp Leu Pro Ser
            210                 215                 220

Leu Gly Leu Thr Leu Val Asn Val Thr Ser Asp Leu Asn Lys Lys Asn
225                 230                 235                 240

Val Thr Cys Trp Ala Glu Asn Asp Val Gly Arg Ala Glu Val Ser Val
                 245                 250                 255

Gln Val Ser Val Ser Phe Pro Ala Ser Val His Leu Gly Lys Ala Val
            260                 265                 270

Glu Gln His His Trp Cys Ile Pro Phe Ser Val Asp Gly Gln Pro Ala
            275                 280                 285

Pro Ser Leu Arg Trp Phe Phe Asn Gly Ser Val Leu Asn Glu Thr Ser
290                 295                 300

Phe Ile Phe Thr Gln Phe Leu Glu Ser Ala Leu Thr Asn Glu Thr Met
305                 310                 315                 320

Arg His Gly Cys Leu Arg Leu Asn Gln Pro Thr His Val Asn Asn Gly
                 325                 330                 335

Asn Tyr Thr Leu Leu Ala Ala Asn Pro Tyr Gly Gln Ala Ala Ala Ser
            340                 345                 350

Ile Met Ala Ala Phe Met Asp Asn Pro Phe Glu Phe Asn Pro Glu Asp
            355                 360                 365

Pro Ile Pro Asp Thr Asn Ser Thr Ser Arg Asp Pro Val Glu Lys Lys
370                 375                 380

Asp Glu Thr
385

<210> SEQ ID NO 27
<211> LENGTH: 382
<212> TYPE: PRT
<213> ORGANISM: Artificial Sequence
<220> FEATURE:
<223> OTHER INFORMATION: Synthetic Construct

<400> SEQUENCE: 27

```
Ala Ala Leu Cys Pro Asp Val Cys Cys Pro Arg Gly Pro Ser Gly Leu
 1               5                  10                 15

Leu Cys Thr Arg Pro Gly Ala Leu Asp Arg Leu Arg His Leu Pro Gly
            20                  25                 30

Ile Glu Asn Leu Thr Glu Leu Tyr Leu Glu Asn Gln Asn Leu Gln His
            35                  40                  45

Leu Thr Leu Gly Asp Leu Arg Gly Leu Arg Glu Leu Arg Asn Leu Ala
 50                  55                  60

Ile Val Asn Ser Gly Leu Gln Ser Val Ala Thr Asp Ala Phe Arg Phe
 65              70                  75                  80

Thr Pro Arg Leu Ser His Leu Asn Leu Ser Phe Asn Ala Leu Glu Ser
                85                  90                  95

Leu Ser Trp Lys Thr Val Gln Gly Leu Pro Leu Gln Glu Leu Val Leu
            100                 105                110

Ser Gly Asn Ser Leu Arg Cys Ser Cys Ala Leu Arg Trp Leu Gln Arg
            115                 120                125

Trp Glu Glu Glu Gly Leu Ala Gly Val Arg Glu Gln Lys Leu Arg Cys
130                 135                 140

Ser Glu Ser Glu Pro Leu Ala Leu Met Pro Asn Ala Ser Cys Gly Met
145                 150                 155                 160

Pro Thr Leu Lys Val Gln Met Pro Asn Gly Ser Val Asp Val Gly Asp
                165                 170                 175

Ser Val Phe Leu Gln Cys Gln Val Glu Gly Gln Gly Leu Glu Lys Ala
                180                 185                 190

Gly Trp Ser Leu Thr Glu Leu Glu Glu Leu Ala Thr Val Met Ile Gln
            195                 200                 205

Lys Ser Glu Asp Leu Pro Thr Leu Arg Leu Thr Leu Ala Asn Val Thr
            210                 215                 220

Ser Asp Leu Asn Arg Lys Asn Val Thr Cys Trp Ala Glu Asn Asp Val
225                 230                 235                 240

Gly Arg Thr Glu Val Ser Val Gln Val Asn Val Ser Phe Pro Ala Ser
                245                 250                 255

Val Gln Leu His Thr Ala Val Glu Met His His Trp Cys Ile Pro Phe
            260                 265                 270

Ser Val Asp Gly Gln Pro Ala Pro Ser Leu His Trp Leu Phe Asn Gly
            275                 280                 285

Ser Val Leu Asn Glu Thr Ser Phe Ile Phe Thr Glu Phe Leu Glu Pro
290                 295                 300

Ala Ala Asn Glu Thr Met Arg His Gly Cys Leu Arg Leu Asn Gln Pro
305                 310                 315                 320

Thr His Val Asn Asn Gly Asn Tyr Thr Leu Leu Ala Thr Asn Pro Ser
                325                 330                 335

Gly Gln Ala Ala Ala Ser Ile Met Ala Ala Phe Met Asp Asn Pro Phe
            340                 345                 350

Glu Phe Asn Pro Glu Asp Pro Ile Pro Val Ser Phe Ser Pro Val Asp
            355                 360                 365

Ala Asn Ser Thr Ser Gly Asp Pro Val Glu Lys Lys Asp Glu
370                 375                 380
```